US011197689B2

(12) United States Patent
Gyrn

(10) Patent No.: US 11,197,689 B2
(45) Date of Patent: Dec. 14, 2021

(54) INSERTER FOR SIMULTANEOUS INSERTION OF MULTIPLE TRANSCUTANEOUS PARTS

(71) Applicant: UNOMEDICAL A/S, Birkerød (DK)

(72) Inventor: Steffen Gyrn, Ringsted (DK)

(73) Assignee: UNOMEDICAL A/S, Birkerod (DK)

(*) Notice: Subject to any disclaimer, the term of this patent is extended or adjusted under 35 U.S.C. 154(b) by 633 days.

(21) Appl. No.: 14/363,282

(22) PCT Filed: Sep. 26, 2012

(86) PCT No.: PCT/EP2012/068928
§ 371 (c)(1),
(2) Date: Jun. 5, 2014

(87) PCT Pub. No.: WO2013/050277
PCT Pub. Date: Apr. 11, 2013

(65) Prior Publication Data
US 2015/0164545 A1  Jun. 18, 2015

Related U.S. Application Data

(60) Provisional application No. 61/543,406, filed on Oct. 5, 2011.

(51) Int. Cl.
*A61B 17/34* (2006.01)
*A61M 5/158* (2006.01)
*A61B 5/00* (2006.01)

(52) U.S. Cl.
CPC ........ *A61B 17/3403* (2013.01); *A61B 5/6847* (2013.01); *A61B 17/3421* (2013.01);
(Continued)

(58) Field of Classification Search
CPC ................................. A61B 17/3403
See application file for complete search history.

(56) References Cited

U.S. PATENT DOCUMENTS

| 1,592,462 A | 7/1926 | Macgregor |
| 2,047,010 A | 7/1936 | Dickinson |

(Continued)

FOREIGN PATENT DOCUMENTS

| CN | 101018578 A | 8/2007 |
| DE | 4342329 A1 | 6/1994 |

(Continued)

OTHER PUBLICATIONS

PCT/EP2012/068928 International Search Report Completed Nov. 22, 2012.

(Continued)

*Primary Examiner* — Niketa I Patel
*Assistant Examiner* — Nathan A Baldwin
(74) *Attorney, Agent, or Firm* — Taft Stettinius & Hollister LLP; Ryan O. White; Derek B. Lavender

(57) ABSTRACT

An inserter (100) for subcutaneous insertion of multiple transcutaneous parts (212, 222), the multiple transcutaneous parts at least comprising: —a first transcutaneous part (212) comprising a first body (214) from where a first subcutaneous part (216) extends, and—a second transcutaneous part (222) comprising a second body (224) from where a second subcutaneous part (226) extends, wherein the inserter comprises: —support means for guiding the multiple transcutaneous parts during insertion of the multiple transcutaneous parts, and—activation means for activating the inserter, whereby simultaneously insertion of the multiple transcutaneous parts subcutaneously in the patient's skin is initiated.

20 Claims, 14 Drawing Sheets

(52) U.S. Cl.
CPC ..... *A61M 5/158* (2013.01); *A61B 2017/3409* (2013.01); *A61M 2005/1585* (2013.01)

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht et al. |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van Den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig, Jr. et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |

(56) References Cited

U.S. PATENT DOCUMENTS

| | | |
|---|---|---|
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili et al. |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple, Jr. |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | Vanantwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. et al. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse, Jr. et al. |
| 6,378,218 B2 | 4/2002 | Sigwart et al. |
| 6,379,335 B1 | 4/2002 | Rigon et al. |
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Roenborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |

(56) References Cited

U.S. PATENT DOCUMENTS

| | | |
|---|---|---|
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher et al. |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. et al. |
| 7,322,473 B2 | 1/2008 | Fux |
| 7,407,491 B2 | 8/2008 | Fangrow, Jr. et al. |
| 7,407,493 B2 | 8/2008 | Cane et al. |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III et al. |
| 8,303,549 B2 | 11/2012 | Mejlhede et al. |
| 8,945,057 B2 | 2/2015 | Gyrn et al. |
| 9,211,379 B2 | 12/2015 | Mejlhede et al. |
| 10,071,210 B2 | 9/2018 | Gray |
| 10,292,641 B2 | 5/2019 | Bureau et al. |
| 10,369,274 B2 | 8/2019 | O'Connor et al. |
| 10,376,638 B2 | 8/2019 | Levesque et al. |
| 10,434,245 B2 | 10/2019 | Yodfat et al. |
| 10,434,247 B2 | 10/2019 | Cole et al. |
| 10,434,253 B2 | 10/2019 | DiPerna et al. |
| 10,434,285 B2 | 10/2019 | Schoonmaker et al. |
| 10,438,696 B2 | 10/2019 | Shapley et al. |
| 10,441,356 B2 | 10/2019 | Zarins et al. |
| 10,441,775 B2 | 10/2019 | Schriver et al. |
| 10,449,290 B2 | 10/2019 | Shapley et al. |
| 10,463,785 B2 | 11/2019 | Dewey |
| 10,463,791 B2 | 11/2019 | Shergold et al. |
| 10,471,203 B2 | 11/2019 | Chappel et al. |
| 10,478,550 B2 | 11/2019 | Hadvary et al. |
| 10,478,552 B2 | 11/2019 | Cronenberg et al. |
| 10,478,554 B2 | 11/2019 | Bazargan et al. |
| 10,478,555 B2 | 11/2019 | Radojicic |
| 10,485,937 B2 | 11/2019 | Yodfat et al. |
| 10,493,201 B2 | 12/2019 | Cole et al. |
| 10,493,202 B2 | 12/2019 | Hayter |
| 10,493,203 B2 | 12/2019 | Yodfat et al. |
| 10,500,352 B2 | 12/2019 | Grant et al. |
| 10,507,316 B2 | 12/2019 | Fielder et al. |
| 10,532,159 B2 | 1/2020 | Tornsten et al. |
| 10,532,835 B2 | 1/2020 | Chong et al. |
| 10,537,681 B2 | 1/2020 | Tan-Malecki et al. |
| 10,539,481 B2 | 1/2020 | Plahey et al. |
| 10,542,936 B2 | 1/2020 | Goldberg et al. |
| 10,549,029 B2 | 2/2020 | Agard et al. |
| 10,549,033 B2 | 2/2020 | Shimizu |
| 10,549,034 B2 | 2/2020 | Eggert et al. |
| 10,549,036 B2 | 2/2020 | Starkweather et al. |
| 10,549,079 B2 | 2/2020 | Burton et al. |
| 10,556,059 B2 | 2/2020 | Cross et al. |
| 10,556,063 B2 | 2/2020 | Murphy, Jr. et al. |
| 10,561,785 B2 | 2/2020 | Roy et al. |
| 10,561,789 B2 | 2/2020 | Mastrototaro et al. |
| 10,561,826 B2 | 2/2020 | Amano et al. |
| 10,569,011 B2 | 2/2020 | Dilanni et al. |
| 10,569,012 B2 | 2/2020 | Schabbach et al. |
| 10,576,204 B2 | 3/2020 | Estes et al. |
| 10,583,241 B2 | 3/2020 | Wu et al. |
| 10,583,247 B2 | 3/2020 | Mandro |
| 10,589,023 B2 | 3/2020 | Cindrich et al. |
| 10,596,362 B2 | 3/2020 | Fielder et al. |
| 10,617,817 B2 | 4/2020 | Hwang et al. |
| 10,617,820 B2 | 4/2020 | O'Connor et al. |
| 10,625,017 B2 | 4/2020 | Searle et al. |
| 10,632,249 B2 | 4/2020 | Marbet et al. |
| 10,632,257 B2 | 4/2020 | Estes et al. |
| 10,635,784 B2 | 4/2020 | Rubalcaba, Jr. et al. |
| 10,639,418 B2 | 5/2020 | Kamen et al. |
| 10,646,652 B2 | 5/2020 | McCullough et al. |
| 10,646,653 B2 | 5/2020 | Despa et al. |
| 10,653,828 B2 | 5/2020 | Brown et al. |
| 10,653,833 B2 | 5/2020 | Kamen et al. |
| 10,653,835 B2 | 5/2020 | Dobbles et al. |
| 10,661,006 B2 | 5/2020 | Antonio et al. |
| 10,661,007 B2 | 5/2020 | Estes |
| 10,661,067 B2 | 5/2020 | Kodama |
| 10,668,210 B2 | 6/2020 | Kamen et al. |
| 10,668,213 B2 | 6/2020 | Cabiri |
| 10,675,055 B2 | 6/2020 | Chong et al. |
| 10,675,404 B2 | 6/2020 | Pizzochero et al. |
| 10,682,458 B2 | 6/2020 | Wu et al. |
| 10,682,460 B2 | 6/2020 | Adams et al. |
| 10,682,463 B2 | 6/2020 | Kamen et al. |
| 10,685,749 B2 | 6/2020 | Hayter et al. |
| 10,688,243 B2 | 6/2020 | Cabiri |
| 10,688,294 B2 | 6/2020 | Cowan et al. |
| 10,716,893 B2 | 7/2020 | Gray et al. |
| 10,716,895 B2 | 7/2020 | Brewer et al. |
| 10,716,926 B2 | 7/2020 | Burton et al. |
| 10,719,584 B2 | 7/2020 | Drew |
| 10,722,643 B2 | 7/2020 | Gray et al. |
| 10,722,646 B2 | 7/2020 | Cole et al. |
| 10,722,647 B2 | 7/2020 | Gray |

(56) References Cited

U.S. PATENT DOCUMENTS

| | | |
|---|---|---|
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,737,015 B2 | 8/2020 | Estes |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,753,683 B2 | 9/2020 | Gibson et al. |
| 10,758,721 B2 | 9/2020 | Sonderegger et al. |
| 10,765,803 B2 | 9/2020 | Gonnelli |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,220 B2 | 9/2020 | Gray |
| 10,792,440 B2 | 10/2020 | Mandro et al. |
| 10,806,851 B2 | 10/2020 | Rosinko |
| 10,806,854 B2 | 10/2020 | O'Connor et al. |
| 10,814,061 B2 | 10/2020 | Bene et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer et al. |
| 2001/0053889 A1 | 12/2001 | Marggi et al. |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0162518 A1 | 8/2004 | Connelly et al. |
| 2004/0162521 A1* | 8/2004 | Bengtsson ....... A61B 5/150022 604/136 |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia et al. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane et al. |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. et al. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson et al. |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Buetikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen et al. |
| 2006/0069351 A9 | 3/2006 | Safabash et al. |

(56) References Cited

U.S. PATENT DOCUMENTS

| | | |
|---|---|---|
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld et al. |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld et al. |
| 2006/0142698 A1 | 6/2006 | Ethelfeld et al. |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alohas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0083222 A1* | 4/2007 | Schraga ............ A61B 5/150022 606/181 |
| 2007/0088271 A1 | 4/2007 | Richards |
| 2007/0093754 A1 | 4/2007 | Mogensen et al. |
| 2007/0104596 A1 | 5/2007 | Preuthun et al. |
| 2007/0112301 A1 | 5/2007 | Preuthun et al. |
| 2007/0112303 A1 | 5/2007 | Liniger et al. |
| 2007/0124002 A1 | 5/2007 | Estes et al. |
| 2007/0129688 A1 | 6/2007 | Scheurer et al. |
| 2007/0129691 A1 | 6/2007 | Sage et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. et al. |
| 2007/0191770 A1 | 8/2007 | Moberg et al. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0276320 A1* | 11/2007 | Wall ........................ A61M 5/19 604/68 |
| 2007/0282269 A1 | 12/2007 | Carter et al. |
| 2007/0299409 A1 | 12/2007 | Whitbourne et al. |
| 2008/0004515 A1 | 1/2008 | Jennewine |
| 2008/0058692 A1 | 3/2008 | Propp et al. |
| 2008/0200897 A1 | 8/2008 | Hoss et al. |
| 2008/0215035 A1 | 9/2008 | Yodfat et al. |
| 2008/0234630 A1 | 9/2008 | Iddan et al. |
| 2008/0243084 A1* | 10/2008 | DeStefano et al. ... A61M 5/158 604/180 |
| 2008/0269687 A1 | 10/2008 | Chong et al. |
| 2008/0281270 A1* | 11/2008 | Cross ................ A61M 5/14248 604/122 |
| 2008/0312601 A1 | 12/2008 | Cane |
| 2009/0062767 A1 | 3/2009 | Van Antwerp et al. |
| 2009/0326453 A1 | 12/2009 | Adams et al. |
| 2009/0326456 A1* | 12/2009 | Cross ................ A61M 5/1424 604/151 |
| 2010/0004597 A1 | 1/2010 | Gyrn et al. |
| 2010/0022863 A1 | 1/2010 | Mogensen et al. |
| 2010/0022956 A1 | 1/2010 | Tipsmark et al. |
| 2010/0030155 A1* | 2/2010 | Gyrn ................ A61M 5/14248 604/164.08 |
| 2010/0049128 A1 | 2/2010 | McKenzie et al. |
| 2010/0094251 A1 | 4/2010 | Estes |
| 2010/0135831 A1 | 6/2010 | Jacobsen |
| 2010/0137829 A1 | 6/2010 | Nielsen et al. |
| 2010/0145303 A1 | 6/2010 | Yodfat et al. |
| 2010/0168670 A1 | 7/2010 | Srisathapat et al. |
| 2010/0228226 A1* | 9/2010 | Nielsen ................ A61M 5/158 604/506 |
| 2010/0241103 A1 | 9/2010 | Kraft et al. |
| 2010/0262078 A1 | 10/2010 | Blomquist |
| 2011/0040247 A1 | 2/2011 | Mandro et al. |
| 2011/0054399 A1 | 3/2011 | Chong et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0313357 A1 | 12/2011 | Skutnik et al. |
| 2012/0078170 A1 | 3/2012 | Smith et al. |
| 2012/0136300 A1 | 5/2012 | Schoonmaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | O'Connor et al. |
| 2013/0138075 A1 | 5/2013 | Lambert |
| 2013/0226138 A1 | 8/2013 | Sia |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0052096 A1 | 2/2014 | Searle et al. |
| 2014/0054883 A1 | 2/2014 | Lanigan et al. |
| 2014/0127048 A1 | 5/2014 | Diianni et al. |
| 2014/0128815 A1 | 5/2014 | Cabiri et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0074578 A1 | 3/2016 | Xu et al. |
| 2016/0082182 A1 | 3/2016 | Gregory et al. |
| 2016/0144105 A1 | 5/2016 | Hooven et al. |
| 2016/0193407 A1 | 7/2016 | Qin et al. |
| 2016/0243302 A1 | 8/2016 | Gyrn |
| 2017/0246386 A1 | 8/2017 | Gyrn |
| 2017/0351851 A1 | 12/2017 | Wang et al. |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298921 A1 | 10/2019 | Stafford |
| 2019/0307943 A1 | 10/2019 | Franano et al. |
| 2019/0307955 A1 | 10/2019 | Levesque et al. |
| 2019/0307970 A1 | 10/2019 | Kamen et al. |
| 2019/0321545 A1 | 10/2019 | Saint |
| 2019/0321552 A1 | 10/2019 | DiPerna et al. |
| 2019/0336678 A1 | 11/2019 | Rule |
| 2019/0336681 A1 | 11/2019 | Kamen et al. |
| 2019/0343434 A1 | 11/2019 | Varsavsky et al. |
| 2019/0344010 A1 | 11/2019 | Pizzochero et al. |
| 2019/0350501 A1 | 11/2019 | Blomquist et al. |
| 2019/0351134 A1 | 11/2019 | Cook et al. |
| 2019/0358395 A1 | 11/2019 | Olson et al. |
| 2019/0366012 A1 | 12/2019 | Gross et al. |
| 2019/0368484 A1 | 12/2019 | Chappel et al. |
| 2019/0374709 A1 | 12/2019 | Cole et al. |
| 2019/0381241 A1 | 12/2019 | Bryant et al. |
| 2019/0388609 A1 | 12/2019 | Lanigan et al. |
| 2019/0388614 A1 | 12/2019 | Gyrn et al. |
| 2019/0388615 A1 | 12/2019 | Sonderegger et al. |

(56) References Cited

U.S. PATENT DOCUMENTS

| | | |
|---|---|---|
| 2020/0001005 A1 | 1/2020 | Politis et al. |
| 2020/0001007 A1 | 1/2020 | Miesel et al. |
| 2020/0009317 A1 | 1/2020 | Cronenberg et al. |
| 2020/0009319 A1 | 1/2020 | Ludolph |
| 2020/0009331 A1 | 1/2020 | Kamen et al. |
| 2020/0016335 A1 | 1/2020 | DiPerna et al. |
| 2020/0023129 A1 | 1/2020 | Day et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0054822 A1 | 2/2020 | Dewey |
| 2020/0054825 A1 | 2/2020 | Kamen et al. |
| 2020/0054826 A1 | 2/2020 | Diianni et al. |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0078511 A1 | 3/2020 | Focht et al. |
| 2020/0086042 A1 | 3/2020 | Kamen et al. |
| 2020/0086043 A1 | 3/2020 | Saint |
| 2020/0101218 A1 | 4/2020 | Shapley et al. |
| 2020/0101226 A1 | 4/2020 | Rosinko et al. |
| 2020/0138852 A1 | 5/2020 | Chattaraj et al. |
| 2020/0138911 A1 | 5/2020 | Joseph et al. |
| 2020/0147304 A1 | 5/2020 | Crouther et al. |
| 2020/0147305 A1 | 5/2020 | Estes |
| 2020/0168316 A1 | 5/2020 | Kamen |
| 2020/0179602 A1 | 6/2020 | Mazlish |
| 2020/0188580 A1 | 6/2020 | Gregory et al. |
| 2020/0188581 A1 | 6/2020 | Diianni et al. |
| 2020/0206418 A1 | 7/2020 | Gonnelli et al. |
| 2020/0215264 A1 | 7/2020 | Searle et al. |
| 2020/0215273 A1 | 7/2020 | Gibson et al. |
| 2020/0253632 A1 | 8/2020 | Chong et al. |
| 2020/0254174 A1 | 8/2020 | Kruse et al. |
| 2020/0261645 A1 | 8/2020 | Kamen et al. |
| 2020/0268962 A1 | 8/2020 | Gamelin |
| 2020/0272310 A1 | 8/2020 | Vik et al. |
| 2020/0276386 A1 | 9/2020 | Kamen et al. |
| 2020/0306446 A1 | 10/2020 | Kamen et al. |
| 2020/0330679 A1 | 10/2020 | Cronenberg et al. |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338266 A1 | 10/2020 | Estes |

FOREIGN PATENT DOCUMENTS

| | | |
|---|---|---|
| DE | 19631921 A1 | 3/1997 |
| DE | 29905072 U1 | 9/1999 |
| DE | 10117285 A1 | 11/2002 |
| DE | 20320207 U1 | 10/2004 |
| EP | 0272530 A2 | 6/1988 |
| EP | 0117632 B1 | 8/1989 |
| EP | 0239244 B1 | 9/1991 |
| EP | 0451040 A1 | 10/1991 |
| EP | 0615768 A2 | 9/1994 |
| EP | 0652027 A1 | 5/1995 |
| EP | 0657184 A1 | 6/1995 |
| EP | 0744183 A2 | 11/1996 |
| EP | 0747006 A1 | 12/1996 |
| EP | 0799626 A1 | 10/1997 |
| EP | 0544837 B1 | 11/1997 |
| EP | 0688232 B1 | 12/1998 |
| EP | 0937475 A2 | 8/1999 |
| EP | 0651662 B1 | 9/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 0714631 B1 | 12/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| EP | 2691144 A1 | 2/2014 |
| FR | 2725902 A1 | 4/1996 |
| FR | 2752164 A1 | 2/1998 |
| GB | 906574 A | 9/1962 |
| GB | 2088215 A | 6/1982 |
| GB | 2230702 A | 10/1990 |
| GB | 2423267 A | 8/2006 |
| GB | 2450872 A | 1/2009 |
| GB | 2459101 A | 10/2009 |
| JP | H03191965 A | 8/1991 |
| JP | H0751251 A | 2/1995 |
| JP | H08187286 A | 7/1996 |
| JP | H10179734 A | 7/1998 |
| JP | 2002028246 A | 1/2002 |
| RU | 2238111 C2 | 10/2004 |
| SU | 933100 A1 | 6/1982 |
| WO | WO-8101795 A1 | 7/1981 |
| WO | WO-8203558 A1 | 10/1982 |
| WO | WO-9204062 A1 | 3/1992 |
| WO | WO-9305840 A2 | 4/1993 |
| WO | WO-9311709 A1 | 6/1993 |
| WO | WO-9420160 A1 | 9/1994 |
| WO | WO-9519194 A1 | 7/1995 |
| WO | WO-9620021 A1 | 7/1996 |
| WO | WO-9632981 A1 | 10/1996 |
| WO | WO-9826835 A1 | 6/1998 |
| WO | WO-9833549 A1 | 8/1998 |
| WO | WO-9858693 A1 | 12/1998 |
| WO | WO-9907435 A1 | 2/1999 |
| WO | WO-9922789 A1 | 5/1999 |
| WO | WO-9933504 A1 | 7/1999 |
| WO | WO-0002614 A1 | 1/2000 |
| WO | WO-0003757 A1 | 1/2000 |
| WO | WO-0044324 A1 | 8/2000 |
| WO | WO-0112746 A1 | 2/2001 |
| WO | WO-0130419 A2 | 5/2001 |
| WO | WO-0168180 A1 | 9/2001 |
| WO | WO-0172353 A2 | 10/2001 |
| WO | WO-0176684 A1 | 10/2001 |
| WO | WO-0193926 A2 | 12/2001 |
| WO | WO-0202165 A2 | 1/2002 |
| WO | WO-0207804 A1 | 1/2002 |
| WO | WO-0240083 A2 | 5/2002 |
| WO | WO-02053220 A1 | 7/2002 |
| WO | WO-02068014 A2 | 9/2002 |
| WO | WO-02081012 A2 | 10/2002 |
| WO | WO-02081013 A2 | 10/2002 |
| WO | WO-02083206 A2 | 10/2002 |
| WO | WO-02083228 A2 | 10/2002 |
| WO | WO-02094352 A2 | 11/2002 |
| WO | WO-02100457 A2 | 12/2002 |
| WO | WO-02102442 A1 | 12/2002 |
| WO | WO-03015860 A1 | 2/2003 |
| WO | WO-03026728 A1 | 4/2003 |
| WO | WO-03068305 A1 | 8/2003 |
| WO | WO-03075980 A2 | 9/2003 |
| WO | WO-03095003 A1 | 11/2003 |
| WO | WO-2004012796 A1 | 2/2004 |
| WO | WO-2004024219 A1 | 3/2004 |
| WO | WO-2004026375 A1 | 4/2004 |
| WO | WO-2004029457 A1 | 4/2004 |

(56) References Cited

FOREIGN PATENT DOCUMENTS

| | | |
|---|---|---|
| WO | WO2004030726 | 4/2004 |
| WO | WO-2004037325 A1 | 5/2004 |
| WO | WO-2004054644 A1 | 7/2004 |
| WO | WO-2004056412 A2 | 7/2004 |
| WO | WO-2004064593 A2 | 8/2004 |
| WO | WO-2004071308 A1 | 8/2004 |
| WO | WO-2004087240 A1 | 10/2004 |
| WO | WO-2004098683 A1 | 11/2004 |
| WO | WO-2004101016 A1 | 11/2004 |
| WO | WO-2004101071 A2 | 11/2004 |
| WO | WO-2004110527 A1 | 12/2004 |
| WO | WO-2005002649 A1 | 1/2005 |
| WO | WO-2005004973 A1 | 1/2005 |
| WO | WO-2005018703 A2 | 3/2005 |
| WO | WO-2005037184 A2 | 4/2005 |
| WO | WO-2005037350 A2 | 4/2005 |
| WO | WO-2005039673 A2 | 5/2005 |
| WO | WO-2005046780 A1 | 5/2005 |
| WO | WO-2005065748 A1 | 7/2005 |
| WO | WO-2005068006 A1 | 7/2005 |
| WO | WO-2005072795 A2 | 8/2005 |
| WO | WO-2005092410 A1 | 10/2005 |
| WO | WO-2005094920 A1 | 10/2005 |
| WO | WO-2005112800 A2 | 12/2005 |
| WO | WO-2005118055 A1 | 12/2005 |
| WO | WO 2006/009665 | 1/2006 |
| WO | WO-2006003130 A1 | 1/2006 |
| WO | WO-2006015507 A2 | 2/2006 |
| WO | WO-2006015600 A2 | 2/2006 |
| WO | WO-2006024650 A2 | 3/2006 |
| WO | WO-2006032689 A1 | 3/2006 |
| WO | WO-2006032692 A1 | 3/2006 |
| WO | WO-2006061027 A2 | 6/2006 |
| WO | WO-2006061354 A1 | 6/2006 |
| WO | WO-2006062680 A1 | 6/2006 |
| WO | WO-2006062912 A1 | 6/2006 |
| WO | WO-2006075016 A1 | 7/2006 |
| WO | WO-2006077262 A1 | 7/2006 |
| WO | WO-2006077263 A1 | 7/2006 |
| WO | WO-2006089958 A1 | 8/2006 |
| WO | WO-2006097111 A2 | 9/2006 |
| WO | WO-2006108775 A2 | 10/2006 |
| WO | WO-2006120253 A2 | 11/2006 |
| WO | WO-2006121921 A2 | 11/2006 |
| WO | WO-2006122048 A1 | 11/2006 |
| WO | WO-2007000162 A2 | 1/2007 |
| WO | WO-2007002523 A2 | 1/2007 |
| WO | WO-2007020090 A1 | 2/2007 |
| WO | WO-2007065944 A1 | 6/2007 |
| WO | WO-2007071255 A1 | 6/2007 |
| WO | WO-2007071258 A1 | 6/2007 |
| WO | WO-2007093051 A1 | 8/2007 |
| WO | WO-2007093182 A2 | 8/2007 |
| WO | WO-2007122207 A1 | 11/2007 |
| WO | WO-2007140631 A1 | 12/2007 |
| WO | WO-2007140783 A2 | 12/2007 |
| WO | WO-2007140785 A1 | 12/2007 |
| WO | WO-2007141210 A1 | 12/2007 |
| WO | WO2008005780 | 1/2008 |
| WO | WO-2008029280 A2 | 3/2008 |
| WO | WO-2008033702 A1 | 3/2008 |
| WO | WO-2008048631 A1 | 4/2008 |
| WO | WO-2008052545 A1 | 5/2008 |
| WO | WO-2008065646 A1 | 6/2008 |
| WO | WO-2008092782 A1 | 8/2008 |
| WO | WO-2008092958 A2 | 8/2008 |
| WO | WO-2008092959 A1 | 8/2008 |
| WO | WO2008098246 | 8/2008 |
| WO | WO-2008135098 A1 | 11/2008 |
| WO | WO-2008147600 A1 | 12/2008 |
| WO | WO-2008148714 A1 | 12/2008 |
| WO | WO-2008155145 A1 | 12/2008 |
| WO | WO-2008155377 A1 | 12/2008 |
| WO | WO2009004026 | 1/2009 |
| WO | WO-2009007287 A1 | 1/2009 |
| WO | WO-2009010396 A1 | 1/2009 |
| WO | WO-2009010399 A1 | 1/2009 |
| WO | WO-2009016635 A2 | 2/2009 |
| WO | WO-2009033032 A1 | 3/2009 |
| WO | WO-2009039013 A1 | 3/2009 |
| WO | WO-2009098291 A1 | 8/2009 |
| WO | WO-2009098306 A1 | 8/2009 |
| WO | WO-2009101130 A1 | 8/2009 |
| WO | WO-2009101145 A1 | 8/2009 |
| WO | WO-2009103759 A1 | 8/2009 |
| WO | WO-2009106517 A1 | 9/2009 |
| WO | WO-2009144272 A1 | 12/2009 |
| WO | WO-2010003885 A1 | 1/2010 |
| WO | WO-2010003886 A1 | 1/2010 |
| WO | WO-2010030602 A1 | 3/2010 |
| WO | WO-2010034830 A1 | 4/2010 |
| WO | 2010051079 A2 | 5/2010 |
| WO | 2010084268 A1 | 7/2010 |
| WO | WO-2010072664 A1 | 7/2010 |
| WO | WO-2010080715 A1 | 7/2010 |
| WO | WO-2010112521 A1 | 10/2010 |
| WO | WO-2011012465 A1 | 2/2011 |
| WO | WO-2011015659 A1 | 2/2011 |
| WO | WO 2011121023 A1 * 10/2011 ............ A61M 5/158 |
| WO | WO-2012041784 A1 | 4/2012 |
| WO | WO-2012041923 A2 | 4/2012 |
| WO | WO-2012045667 A2 | 4/2012 |
| WO | WO-2013050277 A1 | 4/2013 |
| WO | 2015094945 A1 | 6/2015 |

OTHER PUBLICATIONS

Chinese Patent Application No. 2012800597030 Office Action dated May 26, 2015.
European Patent Application No. 12 766 955.4 Communication dated Mar. 18, 2015.
PCT Patent Application No. PCT/DK2007/050103 International Preliminary Report on Patentability dated Nov. 4, 2008.
U.S. Appl. No. 14/008,483 Notice of Allowance dated May 22, 2018.
U.S. Appl. No. 12/375,849 Office Action dated Feb. 2, 2012.
U.S. Appl. No. 12/375,849 Office Action dated Jan. 31, 2013.
U.S. Appl. No. 12/375,849 Office Action dated Jul. 2, 2012.
U.S. Appl. No. 14/008,483 Office Action dated Oct. 13, 2017.
U.S. Appl. No. 14/363,282 Office Action dated Feb. 20, 2018.
"Why inset®?" inset® infusion set product overview; http://web.archive.org/web/20040906102448/http://www.infusion-set.com/Default.asp?ID=108; (2 pgs) (2004).

* cited by examiner

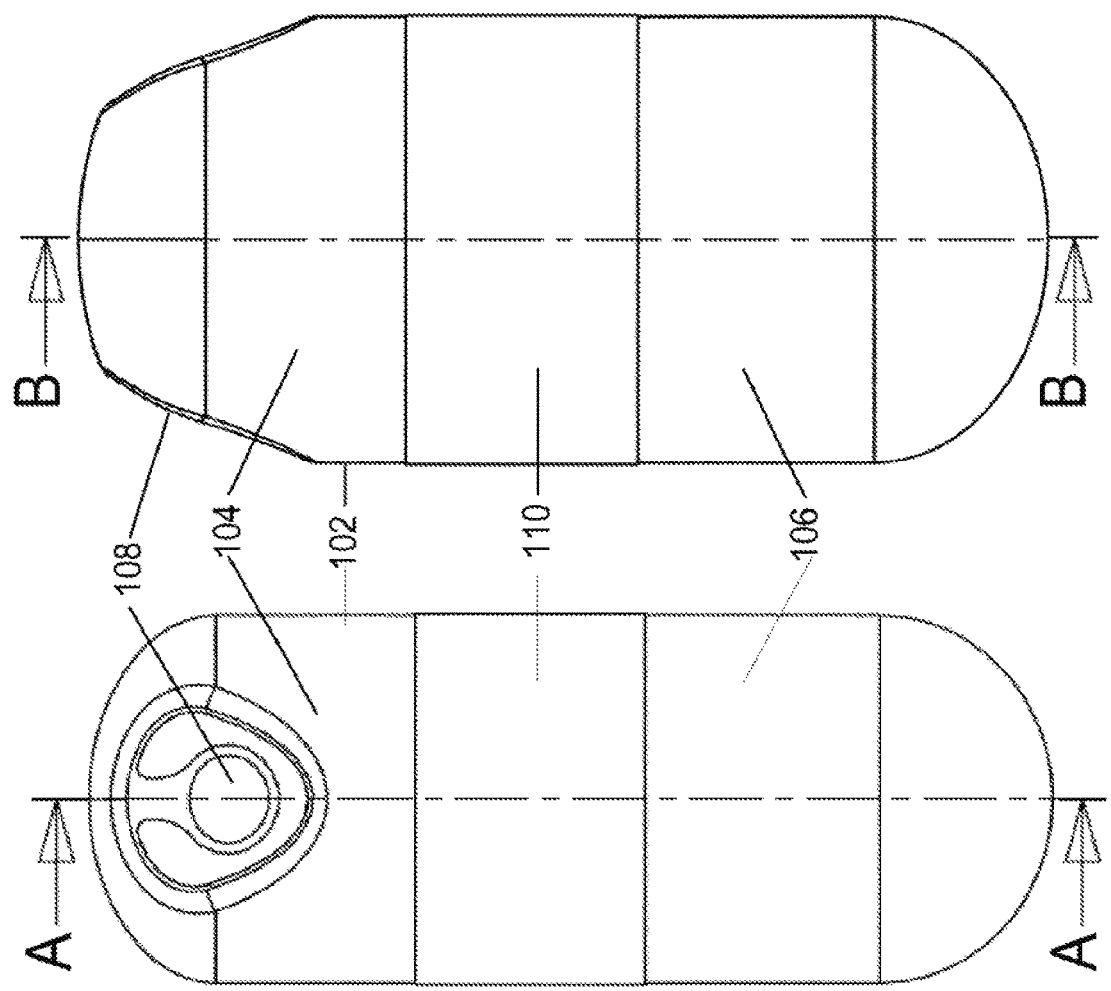

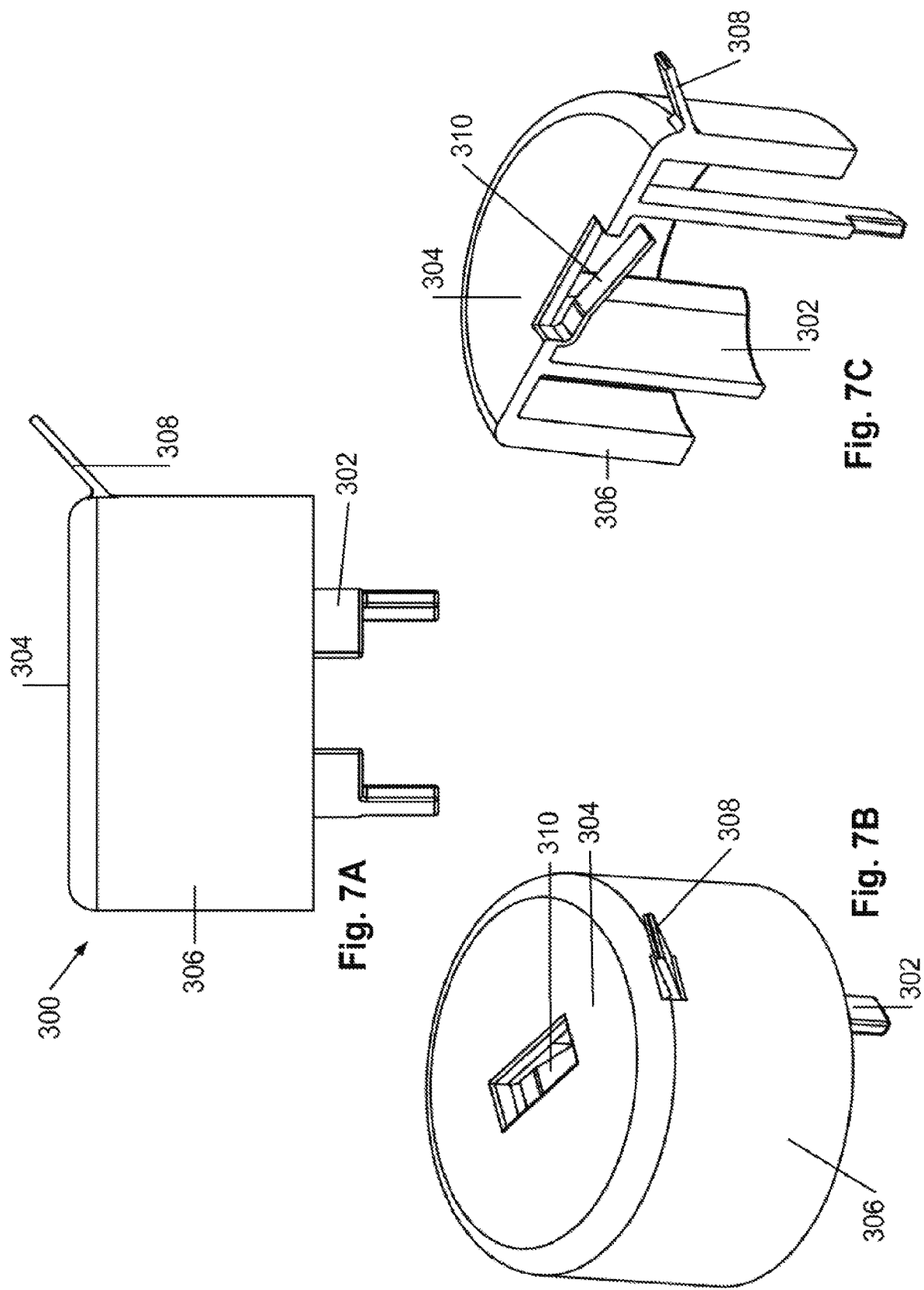

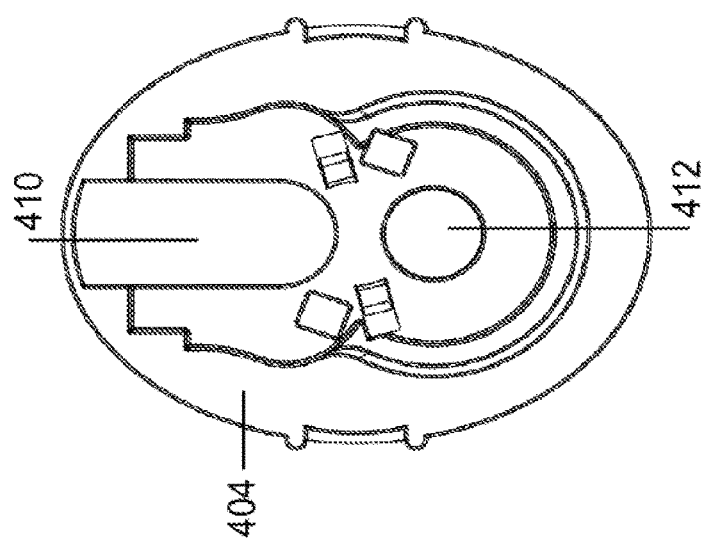
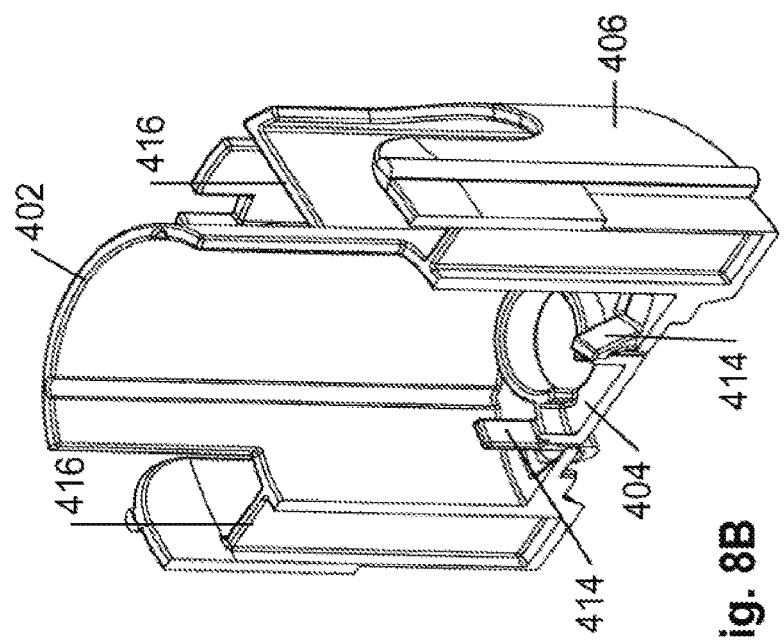
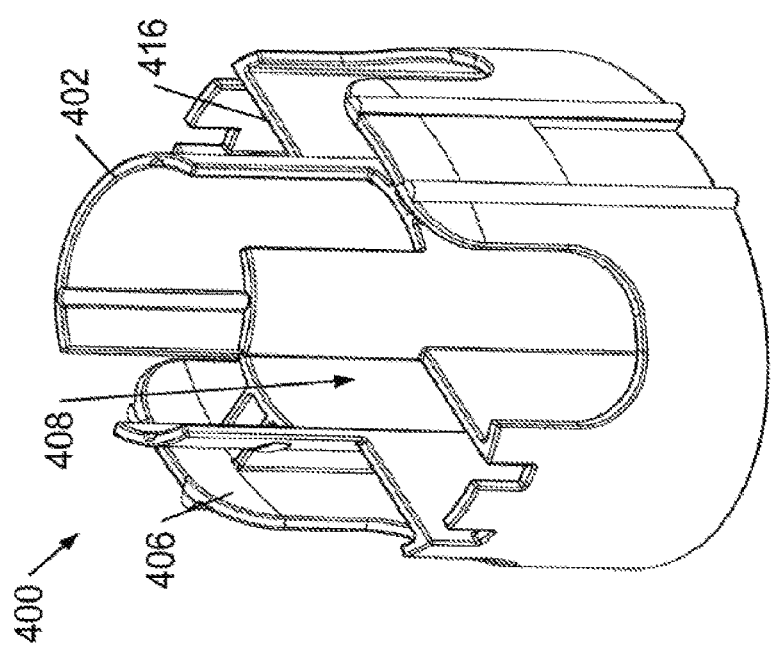

INSERTER FOR SIMULTANEOUS INSERTION OF MULTIPLE TRANSCUTANEOUS PARTS

The invention concerns an inserter for simultaneous insertion of at least two transcutaneous parts.

BACKGROUND

An inserter, also called inserter device or an injector, is commonly used in the medical field for inserting medical devices, such as cannula devices for being connected to infusion sets, sensors or the like, through the skin of a patient in a more or less automated fashion.

Commonly, when using an inserter, the user, i.e. the patient or a treatment provider such as a nurse, a doctor, a relative, or the like, has to apply a force towards the surface of the skin of the patient in order to provide injection of the medical device or a part of the medical device having the form of a needle, a cannula, a sensor, or the like. This can cause physiological or psychological distress and/or discomfort, and may lead to inappropriate application of the medical device. Many people are afraid of sharp objects, such as injection needles and other penetrating devices commonly used for medical treatment and therapy. This fear is often irrational, and it may hamper an appropriate medical treatment. For example in the case of self-medication, a lack of administration of an appropriate dose of a required medical composition can lead to complications, which may even be life-threatening. When treating diabetes, e.g. in juveniles, there is a risk that the required insulin-dose may not be self-administered due to irrational fear of the insertion needle, combined with a general lack of knowledge and awareness concerning the consequences of omitting the correct application of the device and dosage.

A further known issue with insertion of medical devices is the risk of contamination of the penetrating member before or during application. This can easily lead to the introduction of an infection to a patient, e.g. through a contaminated insertion needle. It is further well known that contact with an infected, used needle—especially in hospital environments—can be life-threatening, and the risk of accidental exposure to contaminated material in the form of a used insertion needle must be minimized.

When treating e.g. diabetes it is important to administer the correct amount of insulin to the patients several times during the day. It is therefore essential to regularly monitor the effect of the insulin by e.g. measuring the patient's blood sugar level in order to ensure that the patient receives the correct insulin dosage. Often a cannula part included in an infusion part for administrating insulin to the patient is inserted using one inserter and a sensor device is inserted using a another inserter. The cannula part in the infusion set and the sensor are often inserted at different locations on the patient's body. Thus, consequently, the patient needs to insert two transcutaneous parts individually.

US2008/0004515 discloses an integrated system, wherein a sensor and an on-body patch pump provided with one or more cannulas are combined. The document only describes the combined patch pump/sensor system in broad terms and is silent on how the sensor and the cannula(s) are inserted in the patient's skin.

US2004/0162521 discloses a needle device comprising a housing, a base portion having a mounting surface adapted for application to the skin of a patient, and a plurality of needles. Each needle comprises a distal pointed end adapted to penetrate the skin of a patient. Also, each needle has a first position in which the distal end is retracted relative to the mounting surface and a second position in which the distal end projects from the mounting surface. The US2004/0162521 needle device has to have a height at least corresponding to the length of a needle, as it must contain the needles before and after use in their full length extending in a perpendicular direction relative to the mounting surface. The needle device functions as both as an inserter and as a transcutaneous part device in one. Thus, the entire quite large device is attached onto the patient's skin all the time during use, which is not particularly comfortable for the patient. Further, the subcutaneous parts according to the shown embodiments have to be hard, self-penetrating cannulas provided with a side inlet opening.

Thus, there is an obvious need in the art for a robust, reliable, accurate, safe, hygienic, and user friendly insertion device, which addresses the issues discussed above.

DESCRIPTION OF THE INVENTION

Disclosed herein is an inserter for subcutaneous insertion of multiple transcutaneous parts, the multiple transcutaneous parts at least comprising a first transcutaneous part comprising a first body from where a first subcutaneous part extends, and a second transcutaneous part comprising a second body from where a second subcutaneous part extends, wherein the inserter comprises support means for guiding the multiple transcutaneous parts during insertion of the multiple transcutaneous parts, and activation means for activating the inserter, whereby simultaneously insertion of the multiple transcutaneous parts subcutaneously in the patient's skin is initiated. Thereby is provided a simultaneous insertion of multiple transcutaneous parts, using the compact, robust, reliable, accurate, safe, hygienic, and user friendly inserter according to the above.

In one or more embodiments the support means comprises a functional first part with a proximal first part supporting the multiple transcutaneous parts in a pre-use position.

In one or more embodiments the support means further comprises multiple introducer needles comprising at least a first introducer needle supporting the first subcutaneous part in the pre-use position and a second introducer needle supporting the second subcutaneous part in the pre-use position.

In one or more embodiments the first introducer needle is extending through, partly surrounding or fully surrounding the first subcutaneous part in the pre-use position and the second introducer needle is extending through, partly surrounding or fully surrounding the second subcutaneous part in the pre-use position.

In one or more embodiments the first transcutaneous part and/or the second transcutaneous part is a sensor.

In one or more embodiments the first transcutaneous part and/or the second transcutaneous part is a cannula part.

In one or more embodiments the inserter comprises a cover and the activation means are activation points positioned on the cover.

In one or more embodiments the activation of the inserter is initiated by applying a pressure to activation points in a direction substantially perpendicular to the direction of insertion.

In one or more embodiments the inserter further comprises driving means, wherein upon activation of the inserter, the driving means drives the inserter from the pre-use position to an inserted position, wherein the multiple transcutaneous parts are inserted in the patient's skin in the inserted position.

In one or more embodiments the driving means is a primary spring extending in the direction of insertion.

In one or more embodiments the primary spring upon activation of the inserter translates from a loaded position to an unloaded position, thereby promoting the multiple transcutaneous parts from the pre-use position to the inserted position, where the multiple transcutaneous parts are inserted subcutaneously in the patient's skin.

In one or more embodiments the inserter further comprises a first function part having a proximal first part with a distal surface, the distal surface supporting the primary spring, wherein the primary spring pushes the first functional part from a first position to a second position as the primary spring translates from the loaded position to the unloaded position.

In one or more embodiments the inserter further comprises a release ring, which in the first position engages with the first functional part securing it in the pre-use position and in the second position no longer engages with the functional first part, whereby the primary spring translates from the loaded position to the unloaded position.

In one or more embodiments the inserter after insertion of the transcutaneous part automatically translates to a retracted position where the inserter is separated from the multiple transcutaneous parts.

In one or more embodiments the translation to the retracted position is promoted by retraction means.

In one or more embodiments the retraction means comprises a secondary spring extending in the direction of insertion.

In one or more embodiments the inserter further comprises a functional second part supporting the secondary spring, wherein the secondary spring after insertion of the multiple transcutaneous parts translates from a loaded position to an unloaded position, thereby promoting the functional second part from the inserted position to a retracted position, whereby the inserter is separated from the multiple transcutaneous parts.

In one or more embodiments the distal surface of the proximal first part supports the secondary spring.

In one or more embodiments the multiple introducer needles are attached unreleasably to the functional second part.

BRIEF DESCRIPTION OF THE DRAWINGS

FIGS. 1A-B show the inserter in a shelf position with a marked cut through along the line A-A in FIG. 1A, a marked cut through along the line B-B in FIG. 1B and in a perspective view in FIG. 1C.

FIGS. 7A-C show the cap of the inner inserter part in a front view (FIG. 7A), a perspective view (FIG. 7B) and a perspective cut-through view (FIG. 7C).

FIGS. 8A-C show the housing of the inner inserter part in a perspective view (FIG. 8A), a perspective cut-through view (FIG. 8B) and a 'bottom' view (FIG. 8C).

DETAILED DESCRIPTION

Figure 2A:
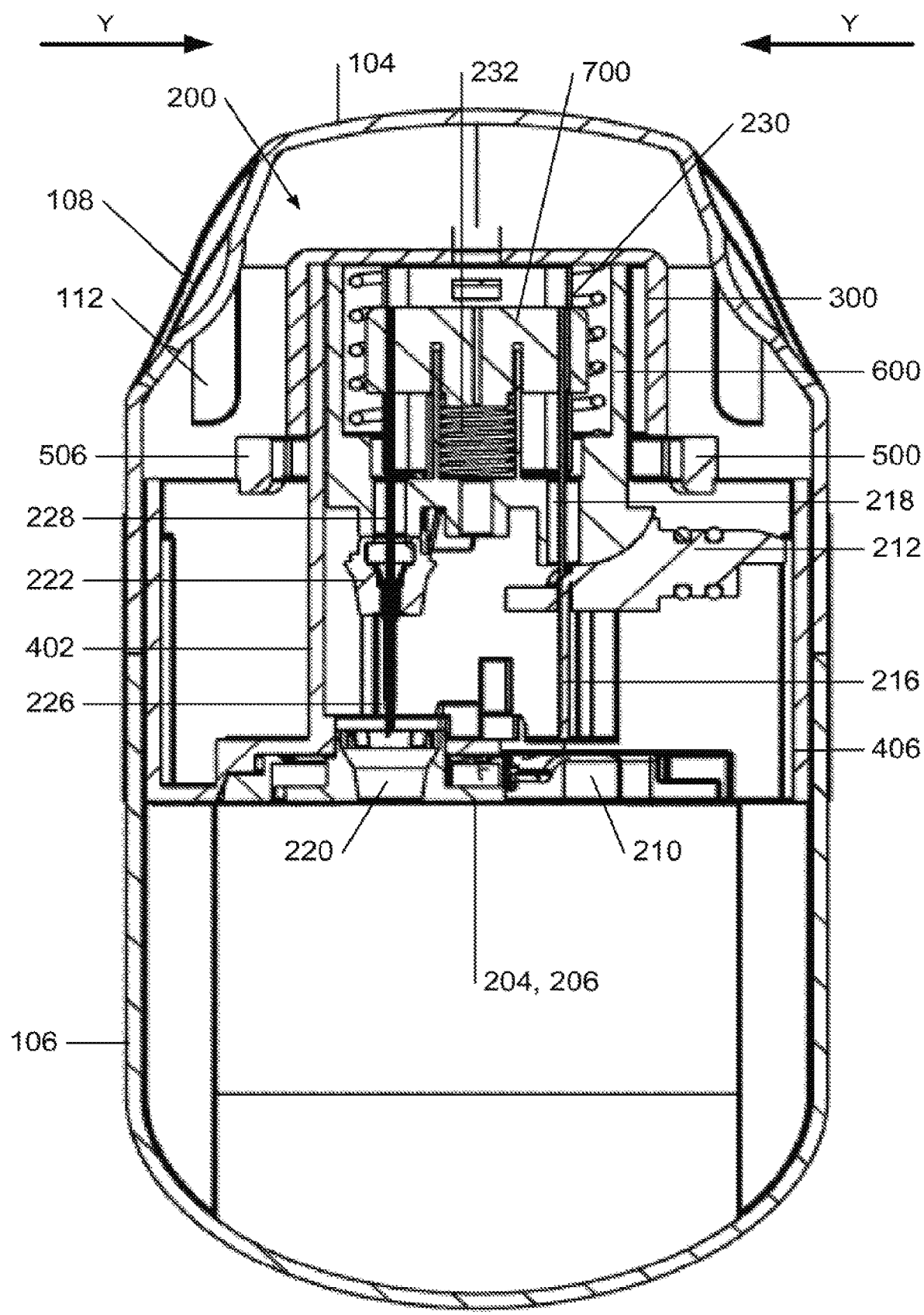
FIG. 2A shows the inserter in a shelf position in a cut through along the line A-A shown in FIG. 1A

In the following description, proximal refers to a surface, part or similar which points towards the patient's skin during insertion and distal refers to a surface, part or similar which points away from the patient's skin during insertion.

FIGS. 1A-C show an inserter 100 according to the invention in a shelf state before use. The embodiment of the inserter 100 has automatic insertion and automatic retraction of multiple introducer needles 218, 228 and is used for placing a base part 204 on the skin of the patient combined with inserting multiple transcutaneous parts 212, 222 subcutaneously in a patient.

The inserter 100 comprises a two-part cover 102 comprising a first cover part 104 and a second cover part 106, wherein the first cover part 104 and the second cover part 106 defines a cavity. Contained inside the cavity is found an inner inserter part 200 comprising several functional parts.

During production, a tamperproof band 110 is placed around the inserter 100 such that it covers the intersection between the first cover part 104 and the second cover part 106. The tamperproof band 110 can be penetrated by sterilizing gas and is therefore placed around the inserter 100 before sterilization. An intact tamperproof band 110 ensures that the second cover part 106 has not been separated from the first cover part 104 after sterilization of the inserter 100, i.e. correct placement of the tamperproof band 110 indicates to the user that the disposable inserter 100 is sterile and ready for use. When using the inserter 100, the tamperproof band 110 is removed thereby allowing the second cover part 106 to be separated from the first cover part 104.

After the tamperproof band 110 and the second cover part 106 have been removed from the first cover part 104, the inserter 100 can be placed on a patient's skin and activated by applying a pressure on the activation points 108 (positioned on the first cover part 104) in the direction towards the inner inserter part 200. The activation points 108 are normally made in a soft material such that they can be pushed towards each other without displacing the remaining part of the first cover part 104.

By applying a pressure to the activation points 108, simultaneously subcutaneous insertion of at least two transcutaneous parts 212, 222 in a patient's skin is initiated. The transcutaneous parts 212, 222 comprise subcutaneous parts 216, 226, which after insertion penetrate the patient's skin subcutaneously. The subcutaneous parts 216, 226 can be e.g. a cannula part and/or a sensor. If the subcutaneous parts 216, 226 are of a soft material, the insertion is normally assisted by using introducer needles 218, 228. The introducer needles 218, 228 can extend through the subcutaneous parts 216, 226 or surround it partly or fully. After insertion of the transcutaneous parts 212, 222, the introducer needles 218, 228 are automatically retracted again. The introducer needles 218, 228 can be omitted if the subcutaneous parts 216, 226 are of a sufficient hard material adequate for penetrating the patient's skin at their own.

Figure 2B:
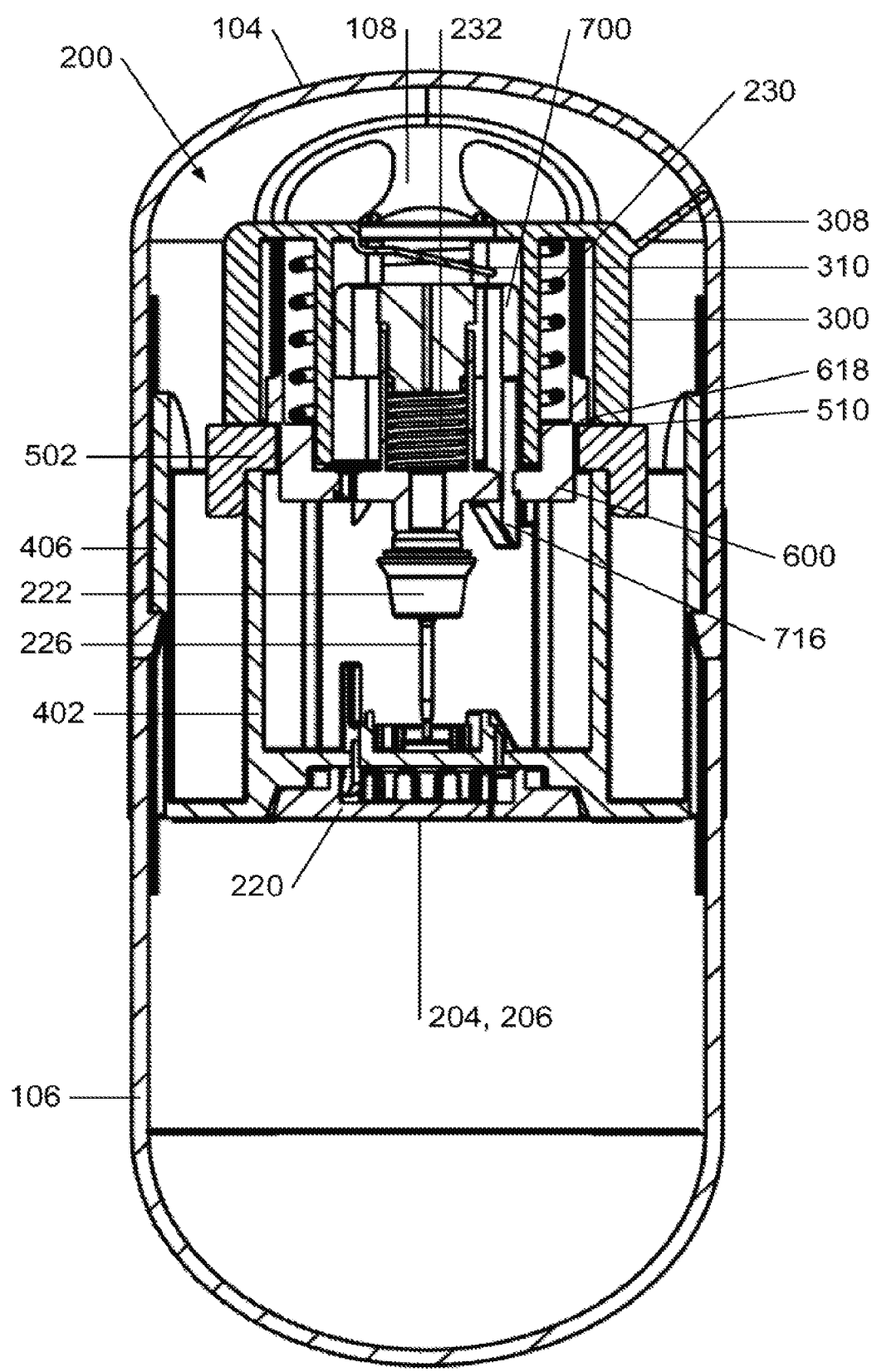
FIG. 2B shows the inserter in a shelf position in a cut through along the line B-B shown in FIG. 1B.
Figure 3A:
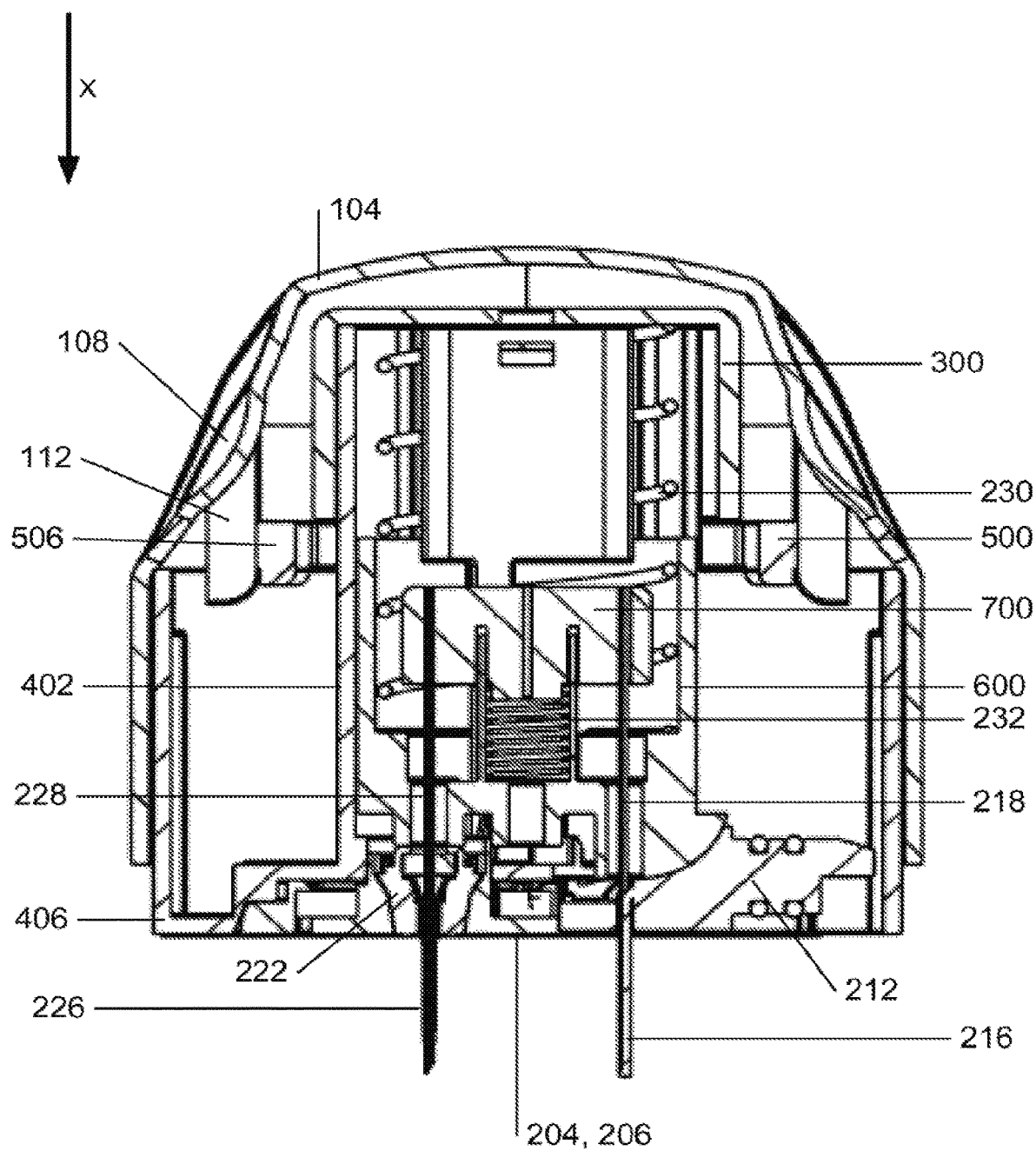
FIG. 3A shows the inserter in an inserted position in a cut through along the line A-A shown in FIG. 1A
Figure 3B:
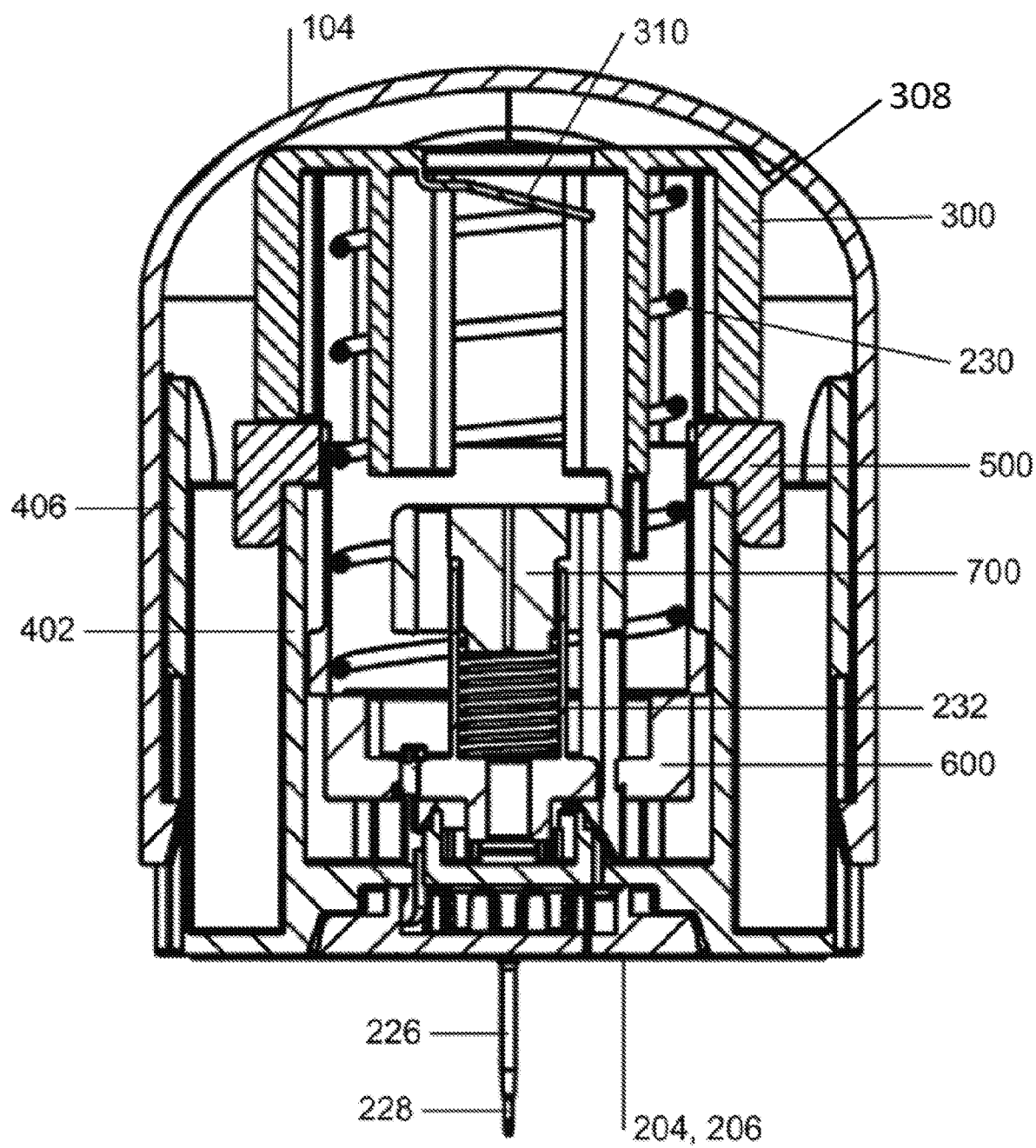
FIG. 3B shows the inserter in an inserted position in a cut through along the line B-B shown in FIG. 1B.
Figure 4A:
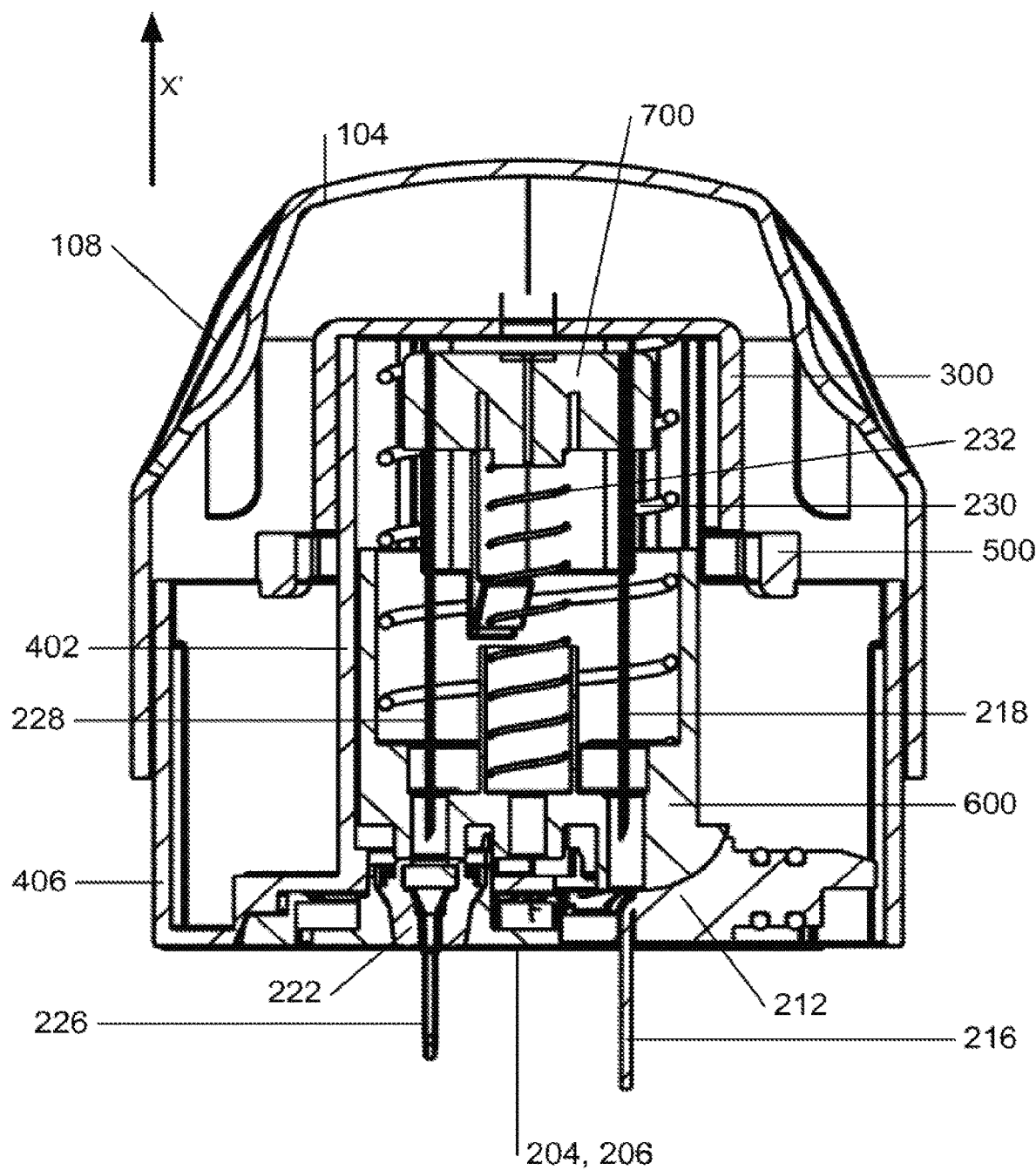
FIG. 4A shows the inserter in a retracted position in a cut through along the line A-A shown in FIG. 1A

FIGS. 2A, 3A and 4A show a cut-through view of the inserter 100 along the A-A line marked in FIG. 1A and FIGS. 2B, 3B and 4B show a cut-through view of the inserter 100 along the B-B line marked in FIG. 1B. Thereby is provided a view of the inner inserter part 200 containing the different functional parts.

In FIGS. 2A-B, the inserter 100 is in the pre-use shelf state before the tamperproof band 110 and the second cover part 106 of the two-part cover 102 have been removed. The inserter 100 shown in this embodiment is also provided with a safety function preventing unintended activation of the inserter 100 prior to use, by insuring that the first cover part 104 cannot move relative to the inner inserter part 200. In order to be able to activate the inserter 100, it is therefore necessary to push the first cover part 104 down until inner activation means having the form of two oppositely positioned protruding parts 112 attached to and/or being part of the inner surface of the first cover part 104 are placed opposite release positions 506 on the release ring 500. Pushing the first cover part 104 down cannot be achieved before the second cover part 106 has been separated from the first cover part 104. In the shelf state shown in FIGS. 2A-B, it is thus not possible to activate the insertion, as the protruding parts 112 are not correctly positioned opposite the release positions 506 on the release ring 500.

FIGS. 3A-B show the inserter 100 after the tamperproof band 110 and the second cover part 106 have been removed and the insertion has been activated by pressing the action points 108. In FIGS. 3A-B, the insertion is at the point where the transcutaneous parts 212, 222 have been inserted in a patient's skin, but the introducer needles 218, 228 have not been retracted.

Figure 4B:
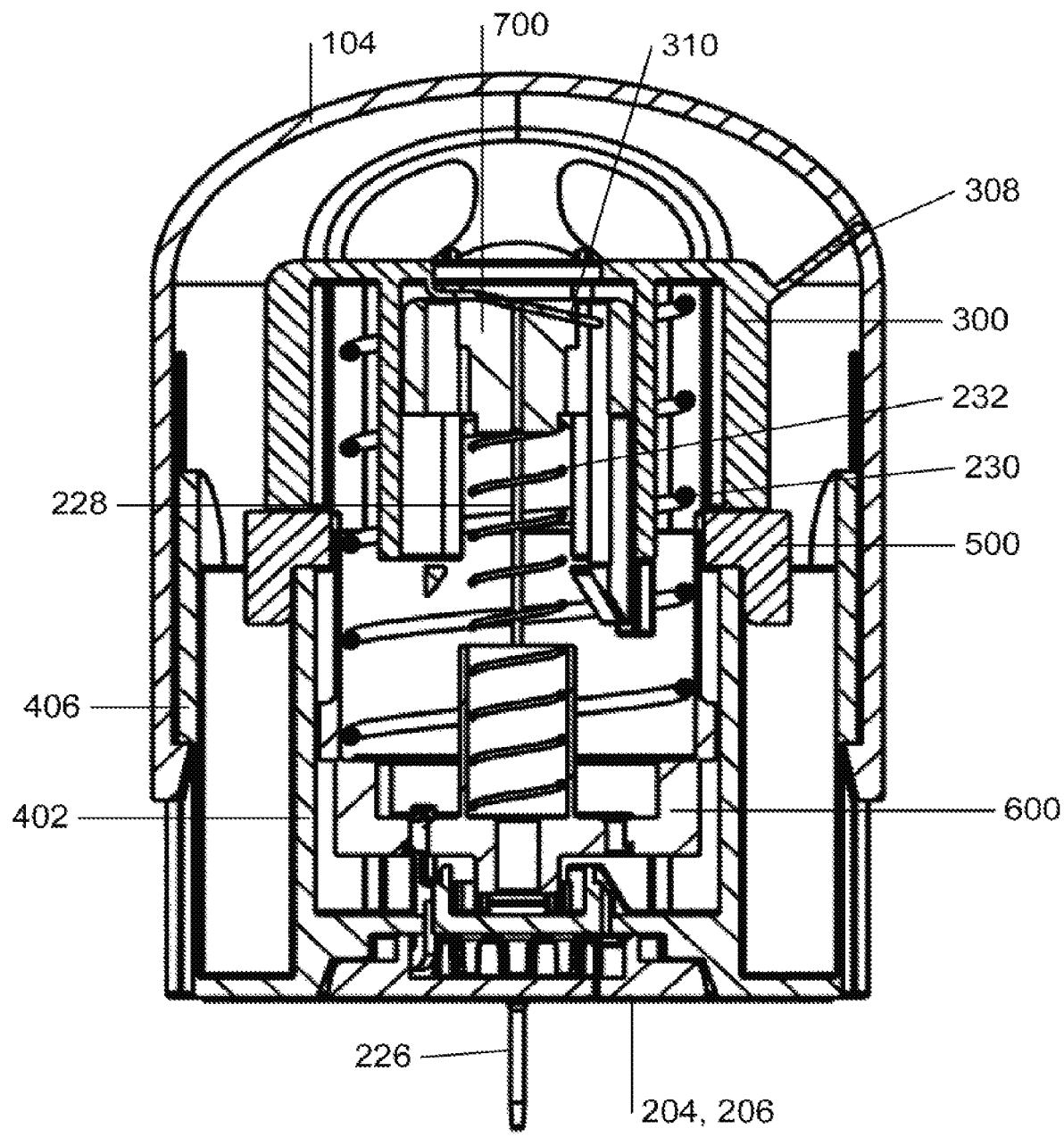
FIG. 4B shows the inserter in a retracted position in a cut through along the line B-B shown in FIG. 1B.

The fully retracted position, where the introducer needles 218, 228 are retracted inside the inner inserter part 200 of the inserter 100 is shown in FIGS. 4A-B.

Figure 5:
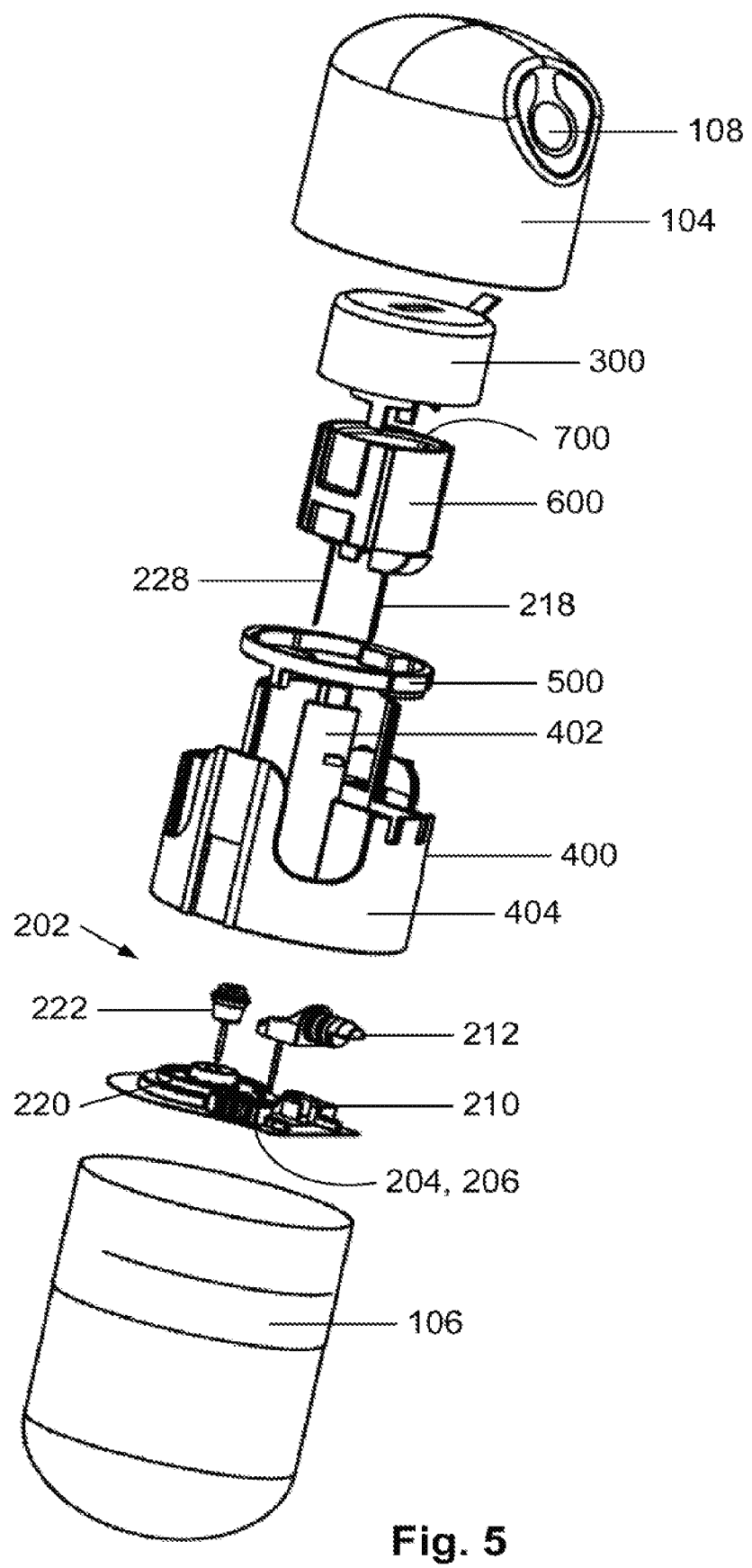
FIG. 5 shows an exploded view of the inserter in the shelf position.
Figure 6:
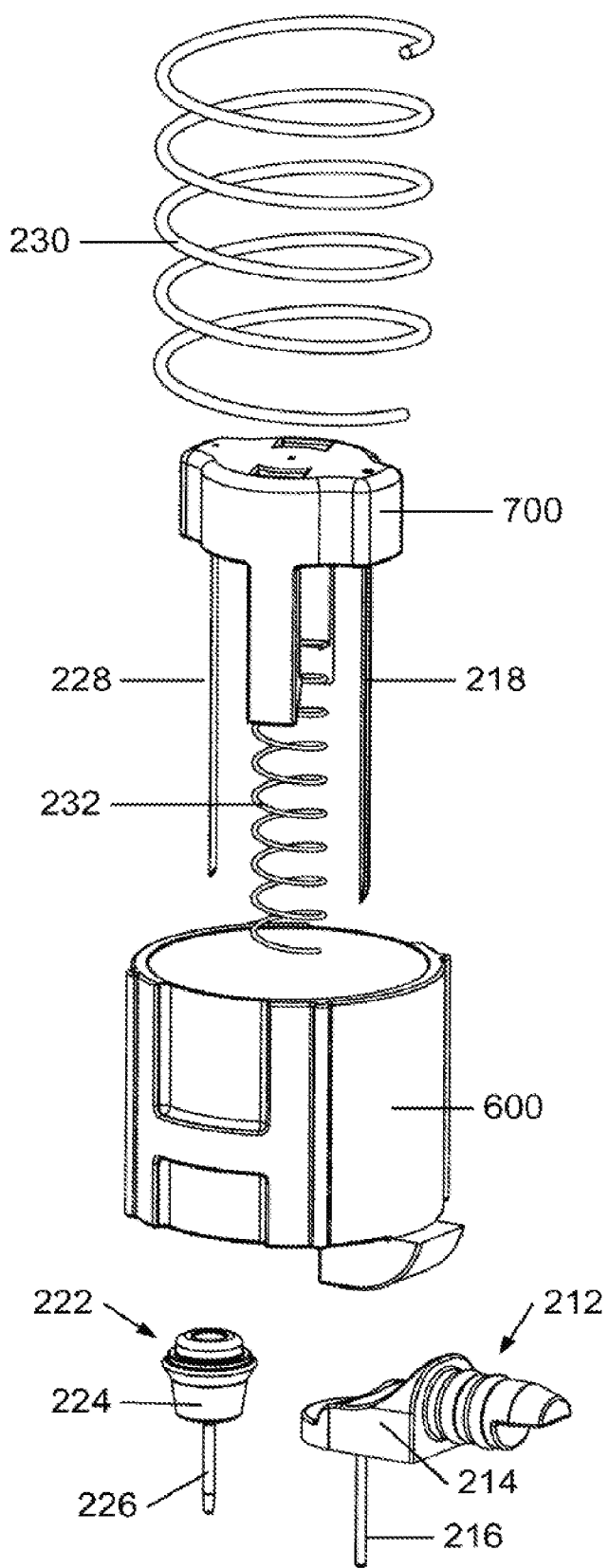
FIG. 6 shows an exploded close-up view of the functional first part, the functional second part, the transcutaneous parts, the springs and the introducer needles.
Figure 9:
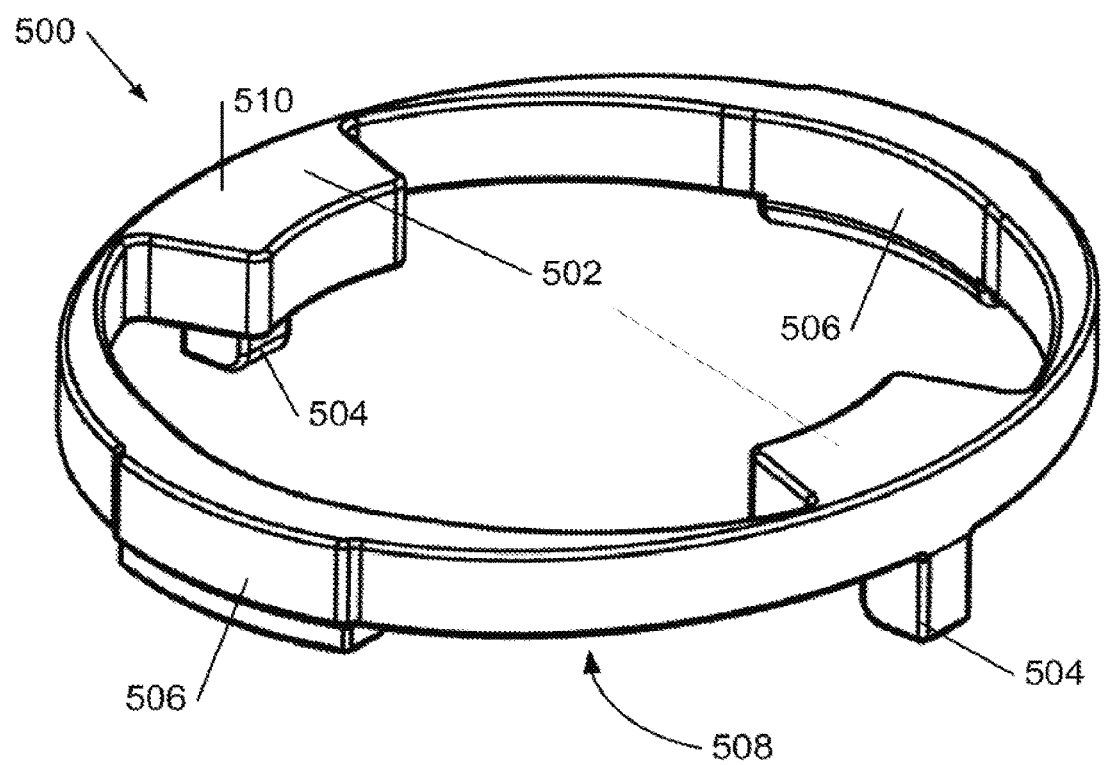
FIG. 9 shows the release ring of the inner inserter part in a perspective view.
Figure 12:
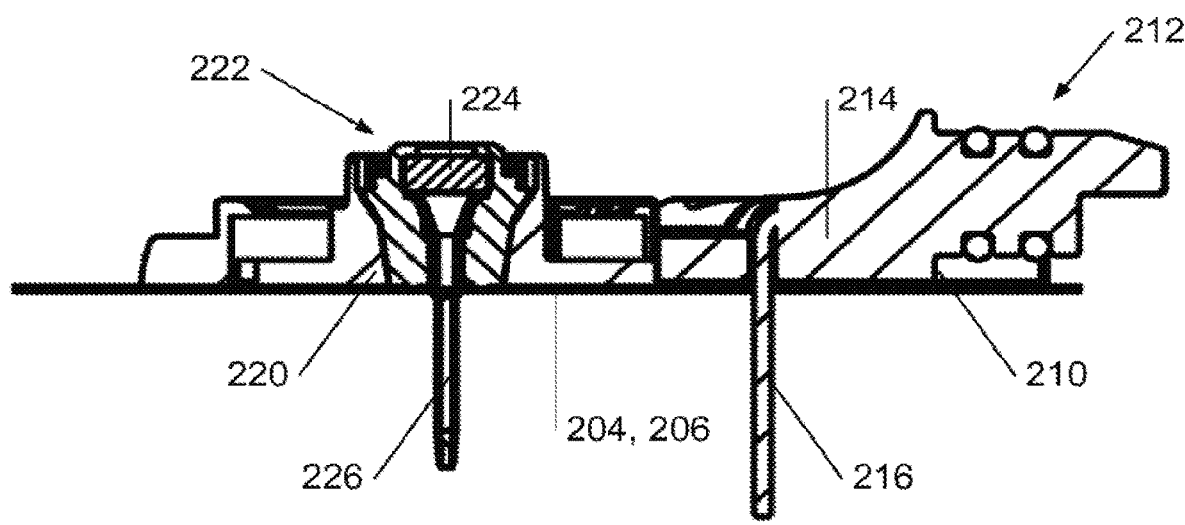
FIG. 12 shows the transcutaneous parts inserter in the base part.
Figure 10C:
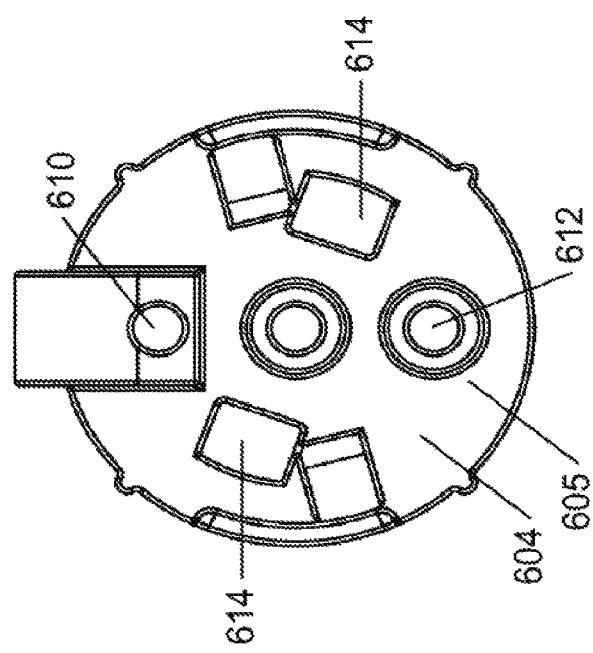
FIGS. 10A-C show the functional first part of the inner inserter part in a perspective view (FIG. 10A), a perspective cut-through view (FIG. 10B) and a 'bottom' view (FIG. 10C).
Figure 10B:
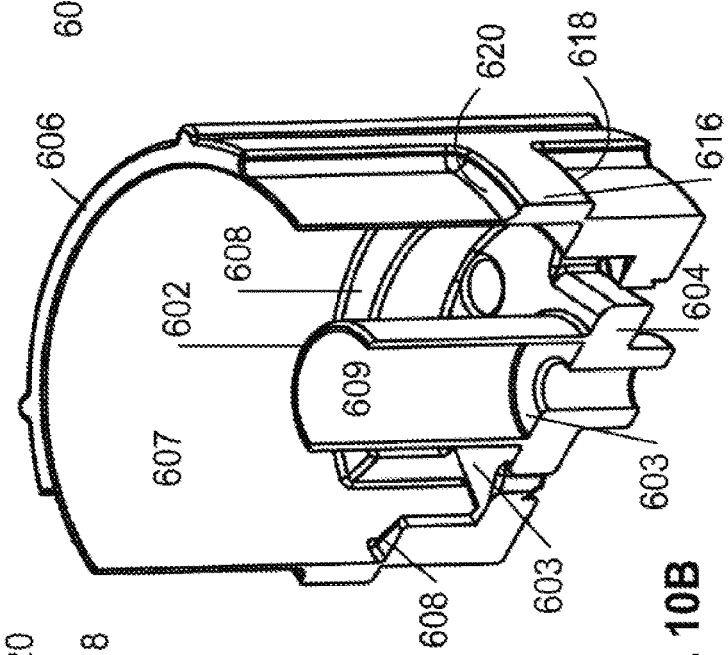
Figure 10A:
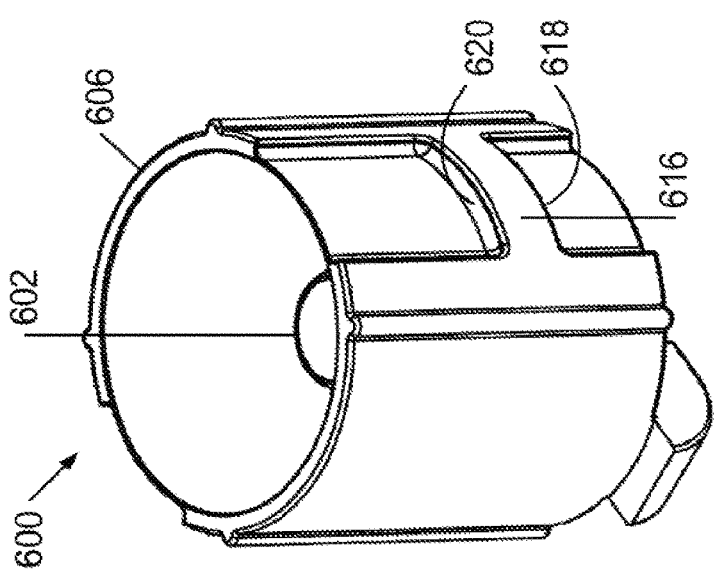
Figure 11B:
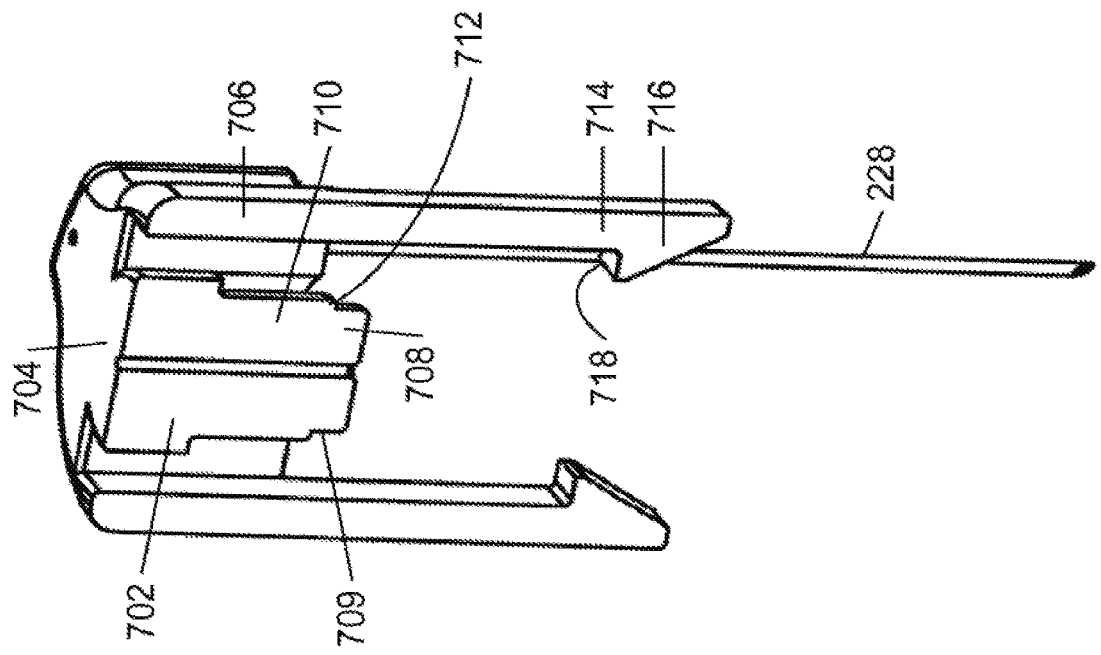
FIGS. 11A-B show the functional second part of the inner inserter part in a perspective view (FIG. 11A) and a perspective cut-through view (FIG. 11B).
Figure 11A:
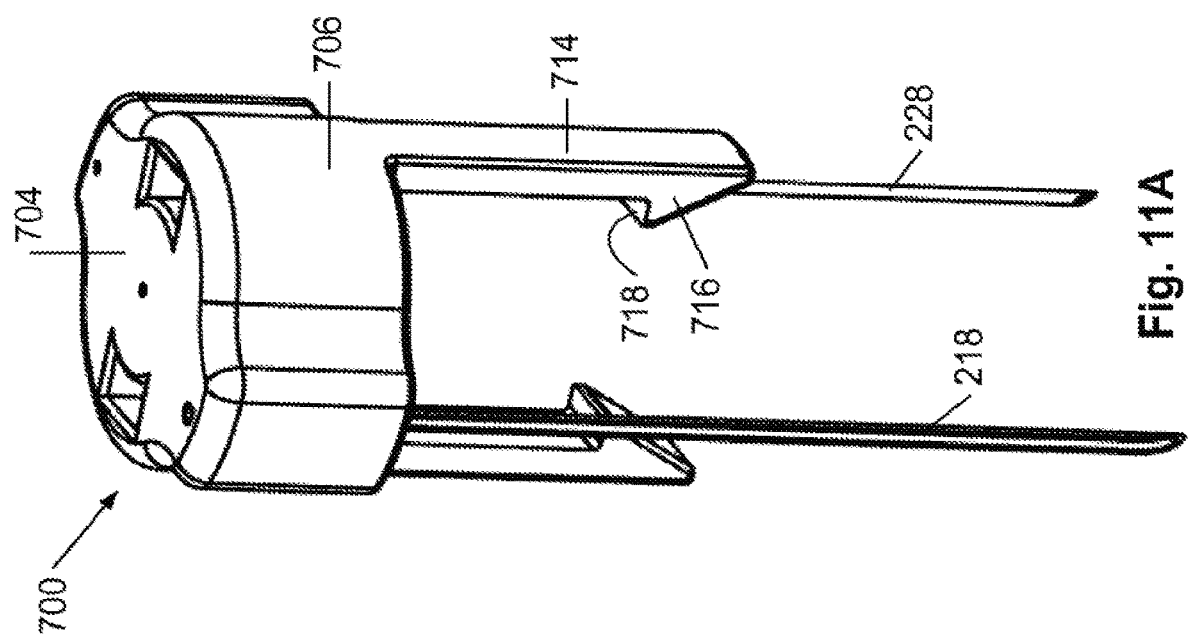

The inner inserter part 200 of the inserter 100 comprises different individual inner functional parts:
- a base part 202 (shown in detail in FIG. 5 and FIG. 12) comprising ports 210, 220 in which the transcutaneous parts 212, 222 are attached during insertion;
- a cap 300 (shown in detail in FIGS. 7A-C);
- a housing 400 (shown in detail in FIGS. 8A-C);
- a release ring 500 (shown in detail in FIG. 9);
- a functional first part 600 (shown in detail in FIGS. 10A-C) functioning as an insertion part, which is released from the release ring during insertion;
- a functional second part 700 (shown in detail in FIGS. 11A-B) functioning as a retraction part, which is released from the insertion part during retraction;
- a primary spring 230 placed between the cap 300 and the functional first part 600 (shown in detail in e.g. FIG. 6);
- a secondary spring 232 placed between the functional second part 700 and the functional first part 600 (shown in detail in e.g. FIG. 6), and
- introducer needles 218, 228 (shown in detail in e.g. FIG. 6 and FIGS. 11A-B) attached to the functional second part 700.

All of the individual parts are normally made of moulded plastic except e.g. the introducer needles 218, 228 which might be made of metal.

The base part 202 is positioned at the proximal end of the inner inserter part 200. The skin facing proximal surface 204 of the base part 202 normally comprises an adhesive surface 206 for ensuring a releasable attachment of the base part 202 to the patient's skin. The adhesive surface 206 can be exposed automatically upon removal of the second cover part 106 or it could be exposed manually e.g. by removing a release paper from the adhesive surface 206 before use. When the adhesive surface 206 is exposed, the proximal end of the inserter 100 comprising the base part 202 is pushed against the skin of the patient.

The base part 202 comprises a first port 210 and a second port 220 for containing the first transcutaneous part 212 and the second transcutaneous part 222, respectively. In the figures, two transcutaneous ports 210, 220 and two transcutaneous parts 212, 222 are shown, but three, four or more 'ports and parts pairs' could also be imagined. In the embodiment shown in the figures, the first transcutaneous part 212 is a sensor and the second transcutaneous part 222 is a cannula for providing fluid connection to a liquid such as e.g. insulin. However, both transcutaneous parts could also be cannulas and/or sensors.

In the shelf position shown in FIGS. 2A-B, the transcutaneous parts 212, 222 are positioned such that their distal surfaces—furthest away from the skin surface—are in contact with the proximal surface 605 of the proximal first part 604 of the functional first part 600. The introducer needles 218, 228 are extending through or surrounding the subcutaneous parts 216, 226 partly or fully. The transcutaneous parts 212, 222 are thereby kept in position due to the friction between the introducer needles 218, 228 and the soft contact parts of the transcutaneous part 212, 222, i.e. the subcutaneous parts 216, 226.

The cap 300 shown in detail in FIGS. 7A-C is positioned at the distal end of the inner inserter part 200 furthest away from the base part 202. The cap 300 comprises an inner cap part 302, a distal cap part 304 being substantially parallel to the surface of the patient's skin, and an outer cap part 306. The inner cap part 302 is tube-shaped with the tube extending in the direction of insertion, and supports a primary spring 230 positioned around the inner cap part 302. The primary spring 230 is further supported at its distal end by the proximal surface of the distal cap part 304.

The cap 300 further comprises a first cap spring 308, which is placed between the cap 300 and an inner surface of the first cover part 104. The first cap spring keeps the first cover part 104 pushed away from the cap 300 in the shelf position. This necessitates an additional action from the user when the inserter 100 is to be activated, namely pushing the first cover part 104 towards the cap 300 in order for the protruding parts 112 of the first cover part 104 to be correctly positioned opposite the release positions 506 on the release ring 500. Thus, the user needs to push the first cover part 104 in the direction towards the patient's skin before insertion can be activated by pressing the at least one activation point 108. This is an easily performed and a natural thing to do for the user, especially if the user is the patient him/her self. As pushing the first cover part 104 in the direction of the patient's skin does not activate the subcutaneous insertion itself, the psychological barrier often associated with pressing a needle through the skin, is not a problem with this inserter 100, as the insertion step is initiated by applying a pressure in a direction parallel to the surface of the skin (direction Y shown in FIG. 2A), i.e. a direction perpendicular to the direction of insertion (direction X shown in FIG. 3A).

In FIG. 3B, the first cap spring 308 is not extending out of the inserter.

The distal cap part 304 may further comprise a second cap spring 310, which reduces sound when the retraction takes place. In the shown embodiment the second cap spring 310 is a flat spring made of same material as the cap 300 and an integrated part of the cap 300.

The housing 400 shown in detail in FIGS. 8A-B comprises an inner housing part 402, a proximal housing part 404 and an outer housing part 406. The inner housing part 402 is shaped as a not fully closed tube extending in the direction of insertion (direction X shown in FIG. 3A).

The proximal housing part 404—being substantially parallel to the surface of the patient's skin—comprises a first opening 410 and a second opening 412 for the first port 210 and the second port 220 of the base part 202, respectively. There is also an opening 408 in the tube-shaped inner housing part 402 in order to facilitate room for the sensor port 210. The openings 410, 412 are so small that is not possible for a user to put a finger through one of the openings 410, 412 and e.g. get in contact with the introducer needles 218, 228.

The distal portion of the inner housing part 402 is positioned in between the inner cap part 302 (where around the distal end of the primary spring 230 is positioned) and the outer cap part 306. The inner housing part 402 is further engaging with the proximal surface of the distal cap part 304. The distal portion of the outer housing part 402 is parallel with and engaging with the proximal portion of the first cover part 104.

Inside the inner housing part 402 is found the release ring 500 and the functional first part 600, the latter again enclosing the functional second part 700 in the shelf position. On a portion of the distal surface of the proximal housing part 404 found inside the inner housing part 402 there are protruding release parts 414 for engaging with corresponding protruding release parts 716 on the functional second part 700 during insertion of the transcutaneous parts 212, 222. The fourth part 400 further comprises distal supports surfaces 416 engaging with and supporting the proximal surface 508 of the release ring 500.

The release ring 500 comprises two protruding release ring parts 502 positioned opposite each other on the release ring 500 and pointing inwardly, and two proximal extending release ring parts 504 each of which is positioned adjacent to the two protruding release ring parts 502. The release ring 500 further comprises two release positions 506 positioned opposite each other on the release ring 500 and displaced approximately 90 degrees in relation to the two protruding release ring parts 502.

The functional first part 600 is functioning as an insertion part, which is released form the release ring during insertion. The functional first part 600 comprises an inner first part 602, a proximal first part 604 being substantially parallel to the surface of the patient's skin, and an outer first part 606. The inner first part 602 and the outer first part 606 are shaped as tubes extending in the direction of insertion (direction X shown in FIG. 3A).

Extending from the distal surface of the proximal first part 604 and adjacent to the outer first part 606 is a ring-shaped protruding ring 608, which supports the proximal end of the primary spring 230. The inner surface 607 of the outer first part 606 ensures that the primary spring 230 can only expand in the direction of insertion/retraction (X, X') and thus not be displaced in the plane perpendicular to the direction of insertion/retraction.

Inside the inner first part 602 and supported by the distal surface 603 of the proximal first part 604 is found the proximal end of the secondary spring 232. The distal surface 603 of the proximal first part 604 thus supports both the primary spring 230 and the secondary spring 232.

The inner surface 609 of the inner first part 602 ensures that the secondary spring 232 can only expand in the direction of insertion/retraction and thus not be displaced in the plane perpendicular to the direction of insertion/retraction.

The proximal first part 604 comprises a first opening 610 and a second opening 612 through which the first introducer needle 218 and the second introducer needle 228, respectively, extends during insertion. The proximal first part 604 further comprises two release openings 614 for engaging with corresponding protruding release parts 716 on the functional second part 700.

On the outside of the outer second part 606 are protruding surface sections 616 comprising a proximal surface 618 and a distal surface 620. In the shelf position, the distal surface 510 of the protruding release ring parts 502 on the release ring 500 engages with the proximal surface 618 of the protruding surface sections 616, thereby securing the primary spring 230 in a loaded position.

The functional second part 700 is functioning as a retraction part, which is retracted from the functional first part 600 after insertion of the transcutaneous parts 212, 222. The functional second part 700 comprises an inner second part 702, a distal second part 704 being substantially parallel to the surface of the patient's skin, and an outer second part 706. The inner second part 702 is shaped as a tube extending in the direction of insertion. The inner second part 702 comprises a first tube section 708 and a second tube section 710, where the diameter of the second tube section 710 is larger than that of the first tube section 708, thereby creating a proximal second tube section surface 712, which supports the distal end of the secondary spring 323. The secondary spring 323 is further supported by the outer surface 709 of the first tube section 708 around which is extends. The first tube section 708 thus ensures that the secondary spring 232 can only expand in the direction of insertion/retraction (X, X') and thus not be displaced in the plane perpendicular to the direction of insertion/retraction.

The distal ends of the introducer needles 218, 228 are secured in the distal second part 704, such that the introducer needles 218, 228 are extending from the proximal surface of the distal second part 704 in the direction of insertion.

The outer second part 706 comprises two legs 714 extending in the direction of insertion. The proximal end of the legs 714 comprises protruding release parts 716 in the shape of inwardly pointing hooks. In the shelf position, the distal surface 718 of the protruding release parts 716 engages with the release openings 614 in the functional first part 600, whereby the functional second part 700 is secured inside the functional first part 600 and the secondary spring 232 is secured in a loaded position.

When using the inserter 100 and positioning the transcutaneous parts 212, 222, the user has to perform the following 7 steps:
1. Remove the tamperproof band 110;
2. Remove the second cover part 106 from the first cover part 104 and expose the adhesive surface 206 of the base part 204;
3. Place the open proximal end of the inserter 100 without the second cover part 106 against the skin of the patient (the adhesive surface 206 of the base part 204 is adhered to the patient's skin during this step);

4. Push the first cover part 104 towards the skin of the patient until it cannot be pushed further;
5. Push at the activation points 108 towards each other, whereby the automatic insertion of the transcutaneous parts 212, 222 followed by retraction of the introducer needles 218, 228 is activated;
6. Remove the inserter device from the patient's skin and optionally re-position the second cover part 106 at the open end of the first cover part 104, and
7. Dispose the used inserter 100 with or without the second cover part 106.

When the insertion of the transcutaneous parts 212, 222 in step S is initiated by pressing the activation points 108 towards each other, the release ring 500 is deformed. By the deformation of the release ring 500, the distance between the release positions 506 positioned opposite each on the release ring 500 is decreased at the same time as the distance between the protruding release ring parts 502 is increased.

As the distance between the protruding release ring parts 502 increases, the distal surface 510 of the protruding release ring parts 502 no longer engages with the proximal surface 618 of the protruding surface sections 616 of the functional first part 600. This allows the primary spring 230 to expand in the direction of insertion (direction X) from the loaded to an unloaded position whereby the functional first part 600—whereto the functional second part 700 is secured—and the transcutaneous parts 212, 222 positioned adjacent to the proximal surface 605 of the fourth part 500 are pushed towards the patient's skin, thus inserting the transcutaneous parts 212, 222 subcutaneously in the patient's skin (see FIGS. 3A-B for the inserted position). During insertion, the transcutaneous parts 212, 222 are locked in the corresponding transcutaneous ports 210, 220 by not shown corresponding locking means on both the transcutaneous parts 212, 222 and the transcutaneous ports 210, 220.

During insertion of the transcutaneous parts 212, 222, the protruding release parts 716 on the functional second part 700 come in direct contact with the protruding release parts 414 on the housing 400. This pushes the protruding release parts 716 outwards and away from each other whereby the distal surface 718 of the protruding release parts 716 is no longer secured in the release openings 614 in the functional first part 600. This again allows the secondary spring 232 to expand from the loaded position to an unloaded position, thereby pushing the functional second part 700 in a direction away from the patient's skin.

As the introducer needles 218, 228 are attached to the functional second part 700, the introducer needles 218, 228 are retracted to a position inside the housing 400 (see FIGS. 4A-B). The introducer needles 218, 228 are thereby no longer exposed and the patient will not be able to see the introducer needles 218, 228 or touch them. The inserter 100 is now separated from the transcutaneous parts 212, 222 and the base part 202 and can consequently be safely removed from the patient's skin and disposed in an ordinary garbage can without there being any risk of repeating the injection procedure.

LIST OF REFERENCES

100 Inserter device
102 Two-part cover
104 First cover part
106 Second cover part
108 Activation points
110 Tamperproof band
112 Protruding parts
200 Inner inserter part
202 Base part
204 Proximal surface of the base part
206 Adhesive surface
210 First port/sensor port
212 First transcutaneous part/sensor part
214 Body of the first transcutaneous part
216 First subcutaneous part
218 First introducer needle
220 Second port/cannula port
222 Second transcutaneous part/cannula part
224 Body of the second transcutaneous part
226 Second subcutaneous part
228 Second introducer needle
230 Primary spring
232 Secondary spring
300 Cap
302 Inner cap part
304 Distal cap part
306 Outer cap part
308 First cap spring
310 Second cap spring
400 Housing
402 Inner housing part
404 Proximal housing part
406 Outer housing part
408 Opening in the inner housing part
410 First opening in the proximal housing part
412 Second opening in the proximal housing part
500 Release ring
502 Protruding release ring part
504 Proximal extending release ring part
506 Release position
508 Proximal surface of the release ring
510 Distal surface of the protruding release ring part
600 Functional first part/insertion part
602 Inner first part
603 Distal surface of the proximal first part
604 Proximal first part
605 Proximal surface of the proximal first part
606 Outer first part
607 Inner surface of the outer first part
608 Protruding ring
609 Inner surface of the inner first part
610 First opening in the proximal first part
612 Second opening in the proximal first part
614 Release openings in the proximal first part
616 Protruding surface section
618 Proximal surface of the protruding surface section
620 Distal surface of the protruding surface section
700 Functional second part/retraction part
702 Inner second part
704 Distal second part
706 Outer second part
708 First tube section of the inner second part
709 Outer surface of the first tube section
710 Second tube section of the inner second part
712 Proximal second tube section surface
714 Leg
716 Protruding release part on the leg
718 Distal surface of the protruding release part
X Direction of insertion
X' Direction of retraction
Y Direction of activation of the inserter

The invention claimed is:

1. An inserter for simultaneous subcutaneous insertion of multiple transcutaneous parts comprising a first transcutaneous part and a second transcutaneous part in a patient, the inserter comprising:
   a cover;
   a support configured to guide the first and second transcutaneous parts during insertion of the multiple transcutaneous parts in the patient, wherein the support includes a first functional part with a proximal first part having a proximal surface, a first projection appended to the proximal surface such that the first projection extends beneath the proximal surface in a vertical direction, and a second projection spaced from the first projection and appended to the proximal surface such that the second projection extends beneath the proximal surface in the vertical direction, wherein the first projection includes an arcuate surface and the second projection includes a flat surface, wherein the first transcutaneous part includes a first transcutaneous surface shaped complementary to the arcuate surface and arranged in contact with the arcuate surface of the first projection, and wherein the second transcutaneous part includes a second transcutaneous surface arranged in contact with the flat surface of the second projection, and
   an activation unit configured to initiate simultaneous subcutaneous insertion of the first and second transcutaneous parts in the patient in a direction perpendicular to a base part of the inserter that is arranged in direct contact with the patient's skin in use of the inserter, wherein the activation unit comprises at least one activation member positioned on or in the cover and the at least one activation member is configured to be activated by pressure in a direction substantially perpendicular to the direction of the simultaneous insertion thereby activating the inserter,
   wherein the inserter has at least one leg defined at least partially around a secondary spring, the at least one leg having a release part defined at a distal end thereof;
   wherein, the release part contacts a corresponding release part of a housing after insertion of the multiple transcutaneous parts and deforms, in response to structural contact between the at least one leg and the corresponding release part, the at least one leg to automatically translate the inserter to a retracted position where the inserter is separated from the multiple transcutaneous parts,
   and wherein the corresponding release part of the housing includes at least one tab sized for structural contact with the release part of the at least one leg.

2. An inserter according to claim 1, wherein the proximal first part supports the first and second transcutaneous parts in a pre-use position.

3. An inserter according to claim 2, wherein the support further comprises multiple introducer needles comprising at least a first introducer needle supporting the first transcutaneous part in the pre-use position and a second introducer needle supporting the second transcutaneous part in the pre-use position.

4. An inserter according to claim 3, wherein the first introducer needle extends through, partly surrounds, or fully surrounds the first transcutaneous part in the pre-use position and the second introducer needle extends through, partly surrounds, or fully surrounds the second transcutaneous part in the pre-use position.

5. An inserter according to claim 1, wherein the first transcutaneous part or the second transcutaneous part is a sensor.

6. An inserter according to claim 1, wherein the first transcutaneous part or the second transcutaneous part is a cannula part.

7. An inserter according to claim 1, wherein the inserter further comprises a driving element, wherein upon activation of the inserter, the driving element drives the inserter from a pre-use position to an inserted position, wherein the first and second transcutaneous parts are inserted subcutaneously in the inserted position.

8. An inserter according to claim 7, wherein the driving element comprises a primary spring extending in the direction of insertion.

9. An inserter according to claim 8, wherein the primary spring upon activation of the inserter translates from a loaded position to an unloaded position to move the first and second transcutaneous parts from the pre-use position to the inserted position, wherein the first and second transcutaneous parts are inserted subcutaneously.

10. An inserter according to claim 9, wherein the proximal first part has a distal surface supporting the primary spring, wherein the primary spring pushes the first functional part from a first position to a second position as the primary spring translates from the loaded position to the unloaded position.

11. An inserter according to claim 10, wherein the inserter further comprises a release ring, wherein when the first functional part is in the first position, the release ring engages with the first functional part to secure the inserter in the pre-use position, and wherein when the first functional part is in the second position, the release ring no longer engages with the first functional part such that the primary spring translates from the loaded position to the unloaded position.

12. An inserter according to claim 1, wherein the translation to the retracted position is promoted by a retraction element.

13. An inserter according to claim 12, wherein the retraction element comprises a secondary spring extending in the direction of insertion.

14. An inserter according to claim 13, wherein the inserter further comprises a second functional part supporting the secondary spring, wherein the secondary spring after activation of the inserter and insertion of the first and second transcutaneous parts translates from a loaded position to an unloaded position to move the second functional part from an inserted position to a retracted position, whereby the inserter is separated from the first and second transcutaneous parts.

15. An inserter according to claim 14, wherein multiple introducer needles are attached unreleasably to the second functional part.

16. An inserter according to claim 13, wherein a distal surface of the proximal first part supports the secondary spring.

17. An inserter assembly, comprising:
   a cover part coupled to a housing and defining an internal cavity;
   a retraction part selectively coupled to an insertion part and positioned at least partially within the internal cavity, wherein the retraction part has at least two introducer needles coupled thereto and the insertion part has at least two transcutaneous parts coupled thereto;

a primary spring positioned between the cover part and the insertion part and configured to provide a biasing force on the insertion part away from the cover part; and a secondary spring positioned between the retraction part and the insertion part;

wherein, an activation point located on an exterior of the cover part is engageable to cause the biasing force of the primary spring to move the retraction part and insertion part away from the cover part in a direction perpendicular to a base part of the inserter assembly that is arranged in direct contact with a patient's skin in use of the inserter assembly;

wherein, the retraction part is movable to contact a release part of the housing to uncouple the retraction part from the insertion part to allow the retraction part to move away from the insertion part by the biasing force of the secondary spring and the introducer needles to separate from the transcutaneous parts, wherein the release part of the housing includes at least one tab sized for structural contact with the retraction part to cause uncoupling of the retraction part from the insertion part and subsequent separation of the introducer needles from the at least two transcutaneous parts, wherein the insertion part includes a ring extending upwardly in a vertical direction from a distal surface of the insertion part and an inner part extending upwardly in the vertical direction from the distal surface that completely surrounds a central axis of the insertion part, wherein the ring is in contact with the primary spring and arranged radially outward of the central axis of the insertion part, wherein the inner part at least partially surrounds the secondary spring, and wherein in a pre-use state of the inserter assembly, the primary spring and the secondary spring are positioned to overlap one another in the vertical direction.

18. The inserter assembly of claim 17, further wherein the retraction part has at least one leg extending therefrom that selectively engages a release opening of the insertion part to selectively couple the retraction part to the insertion part.

19. The inserter assembly of claim 18, further wherein the at least one leg defines a release part that is sized to contact the release part of the housing to thereby deform the at least one leg to uncouple the retraction part from the insertion part.

20. The inserter assembly of claim 17, further wherein the primary spring and secondary spring are defined along a longitudinal axis and the activation point is movable radially towards the longitudinal axis to cause the biasing force of the primary spring to move the retraction part and insertion part away from the cover part.

* * * * *